United States Patent
Lessing et al.

(10) Patent No.: US 11,737,913 B2
(45) Date of Patent: Aug. 29, 2023

(54) SYSTEMS AND METHODS FOR TEMPERATURE-CONTRAST THERAPY

(71) Applicant: KCI Licensing, Inc., San Antonio, TX (US)

(72) Inventors: Marcus Christian Lessing, San Antonio, TX (US); Sandra N Osborne, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 597 days.

(21) Appl. No.: 16/634,467

(22) PCT Filed: Jul. 11, 2018

(86) PCT No.: PCT/US2018/041672
§ 371 (c)(1),
(2) Date: Jan. 27, 2020

(87) PCT Pub. No.: WO2019/022955
PCT Pub. Date: Jan. 31, 2019

(65) Prior Publication Data
US 2021/0085518 A1    Mar. 25, 2021

Related U.S. Application Data

(60) Provisional application No. 62/538,500, filed on Jul. 28, 2017.

(51) Int. Cl.
*A61F 7/00* (2006.01)
*A61F 7/02* (2006.01)
*A61M 1/00* (2006.01)

(52) U.S. Cl.
CPC ............ *A61F 7/0085* (2013.01); *A61F 7/007* (2013.01); *A61F 7/02* (2013.01); *A61M 1/85* (2021.05);
(Continued)

(58) Field of Classification Search
CPC .......... A61F 7/0085; A61F 7/007; A61F 7/02; A61F 2007/0052; A61F 2007/0054;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Wikipedia, PID controller, https://en.wikipedia.org/wiki/PID_controller; accessed Jul. 15, 2022 (Year: 2022).*

(Continued)

*Primary Examiner* — Jonathan T Kuo

(57) ABSTRACT

In one example embodiment, a system for stimulating tissue with the application of temperature-regulated fluid and negative pressure comprises a negative-pressure source adapted to provide negative pressure to a dressing. The system may further comprise a thermoelectric module thermally coupled to a first heat exchange chamber and a second heat exchange chamber and adapted to transfer heat between said heat exchange chambers. The thermoelectric module can be further adapted to maintain a temperature-regulated fluid fluidly coupled to the first heat exchange chamber and the dressing within a predetermined temperature range by adding heat to and extracting heat from the temperature-regulated fluid as it passes through the first heat exchange chamber.

12 Claims, 16 Drawing Sheets

(52) U.S. Cl.
CPC ....... *A61M 1/92* (2021.05); *A61F 2007/0052* (2013.01); *A61F 2007/0054* (2013.01); *A61F 2007/0076* (2013.01); *A61F 2007/0078* (2013.01); *A61F 2007/0093* (2013.01); *A61F 2007/0239* (2013.01); *A61F 2007/0296* (2013.01)

(58) Field of Classification Search
CPC ...... A61F 2007/0076; A61F 2007/0078; A61F 2007/0093; A61F 2007/0239; A61F 2007/0296; A61F 2007/0059; A61F 2007/0095; A61F 2007/0096; A61M 1/85; A61M 1/90; A61M 2205/3368; A61M 2205/3673
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,097,829 A | 3/1992 | Quisenberry |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,895,418 A * | 4/1999 | Saringer ................. F25B 21/02 607/104 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,395,249 B2 * | 7/2016 | Han ................... G05D 23/1919 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0035562 A1* | 2/2012 | Locke ................... A61M 1/962 604/319 |
| 2012/0220960 A1 | 8/2012 | Ruland |
| 2012/0259266 A1* | 10/2012 | Quisenberry ..... A61F 13/00029 604/20 |
| 2014/0072015 A1* | 3/2014 | Han ................... G05D 23/1919 374/179 |

(56) References Cited

U.S. PATENT DOCUMENTS

| | | | |
|---|---|---|---|
| 2014/0163491 | A1 | 6/2014 | Schuessler et al. |
| 2015/0080788 | A1 | 3/2015 | Blott et al. |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2015180804 | A1 | 12/2015 |

OTHER PUBLICATIONS

International Search Report and Written Opinion for corresponding Application No. PCT/US2018/041672, dated Oct. 2018.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, Nos. May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

| TIME | PERCENT CELL COVERAGE FOR HDFa TREATED WITH FOUR DEGREE CELSIUS MEDIA | PERCENT CELL COVERAGE FOR HDFa TREATED WITH TWENTY FIVE DEGREE CELSIUS MEDIA |
|---|---|---|
| 22:38 | 12.1 | 13.8 |
| UNTREATED OVERNIGHT | | |
| 8:38 | 14.3 | 17.4 |
| 9:53 | 16.2 | 16.3 |
| 11:08 | 17.2 | 21.6 |
| 12:38 | 16.8 | 14.6 |
| 15:38 | 20.9 | 15.6 |
| 16:53 | 20.2 | 17.3 |
| 18:08 | 23.7 | 17.1 |
| UNTREATED OVERNIGHT | | |
| 8:08 | 27.1 | 21.1 |
| 9:38 | 29.6 | 19.8 |
| 11:00 | 27.1 | 17 |
| 12:53 | 26.3 | 25.4 |
| 14:53 | 23.2 | 25.1 |
| 16:08 | 24.3 | 31.2 |
| UNTREATED OVERNIGHT | | |
| 9:38 | 31.3 | 40 |
| UNTREATED OVERNIGHT | | |
| 11:38 | 35.3 | 33.6 |
| UNTREATED OVERNIGHT | | |
| UNTREATED OVERNIGHT | | |
| UNTREATED OVERNIGHT | | |
| 13:08 | 65.7 | 67.8 |

FIG. 11A

|  | RELATIVE TO STARTING PERCENT CELL COVERAGE FOR HDFa TREATED WITH FOUR DEGREE CELSIUS MEDIA (1210) | RELATIVE TO STARTING PERCENT CELL COVERAGE FOR HDFa TREATED WITH TWENTY FIVE DEGREE CELSIUS MEDIA (1220) |
|---|---|---|
|  | 100 | 100 |
| TREATED AT 9:23 | 118.1818182 | 126.0869565 |
|  | 133.8842975 | 118.115942 |
| TREATED AT 11:23 | 142.1487603 | 156.5217391 |
|  | 138.8429752 | 105.7971014 |
| TREATED AT 15:38 | 172.7272727 | 113.0434783 |
|  | 166.9421488 | 125.3623188 |
| TREATED AT 18:08 | 195.8677686 | 123.9130435 |
|  | 223.9669421 | 152.8985507 |
| TREATED AT 9:35 | 244.6280992 | 143.4782609 |
|  | 223.9669421 | 123.1884058 |
| TREATED AT 12:38 | 217.3553719  1268 | 184.057971 |
|  | 191.7355372 | 181.884058 |
| TREATED AT 15:38 | 200.8264463 | 226.0869565 |
| TREATED AT 08:38 | 258.677686 | 289.8550725 |
| TREATED AT 09:23 | 291.7355372 | 243.4782609 |
| FINAL PERCENT | 542.9752066 | 491.3043478 |

(1270 labels the leftmost column; FROM FIG. 11A)

FIG. 11B

SYSTEMS AND METHODS FOR TEMPERATURE-CONTRAST THERAPY

RELATED APPLICATION

This application claims the benefit, under 35 U.S.C. § 119(e), of the filing of U.S. Provisional Patent Application Ser. No. 62/538,500, entitled "SYSTEMS AND METHODS FOR TEMPERATURE-CONTRAST THERAPY," filed Jul. 28, 2017, which is incorporated herein by reference for all purposes.

BRIEF SUMMARY

Temperature-contrast therapy generally comprises alternately applying contrasting temperatures through some medium proximate to a tissue site for several cycles within a therapeutic period. For example, temperature-contrast therapy may comprise alternately applying warm and cold fluid to a tissue site. The applications of this treatment can be numerous, and it has been proven to relieve pain and inflammation at a tissue site. Temperature-contrast therapy can also be an effective treatment option for non-chronic wounds, and its benefits can include augmenting and accelerating the growth of new tissue at the wound site. Together, these benefits can increase development of granulation tissue and reduce healing times at the tissue site.

New and useful systems, apparatuses, and methods for applying temperature-contrast therapy to a tissue site are set forth in the appended claims. Illustrative embodiments are also provided to enable a person skilled in the art to make and use the claimed subject matter.

In some embodiments, a system for stimulating healing of a tissue site may apply exogenously heated and cooled fluid for contrast therapy to a tissue site. For example, a system may comprise a thermoelectric module configured to selectively modify the temperature of a therapeutic fluid, and a controller configured to operate the thermoelectric module to regulate the temperature of the therapeutic fluid. The controller may also be configured to provide contrast-instillation therapy, wherein the contrast-instillation therapy comprises periodically modifying the temperature of the therapeutic fluid. In some embodiments, for example, the controller may be configured to deliver therapeutic fluid to a tissue site, and to periodically increase the temperature of the therapeutic fluid. Additionally or alternatively, the controller may be configured to periodically decrease the temperature of the therapeutic fluid. In some embodiments, a negative-pressure source may be adapted to be fluidly coupled to a dressing positioned at a tissue site and used in conjunction with the thermoelectric module and the controller to remove the therapeutic fluid, or to provide contrast-instillation therapy with negative-pressure therapy.

In some embodiments, a system for stimulating healing of tissue with the application of temperature-regulated fluid and negative pressure may comprise a negative-pressure source fluidly coupled to a dressing positioned at a tissue site. The negative-pressure source is generally adapted to maintain negative pressure at the tissue site. The system may further comprise a thermoelectric module, which can be thermally coupled to a first heat exchange chamber and a second heat exchange chamber. The first heat exchange chamber or the second heat exchange chamber may be fluidly coupled to the dressing. The thermoelectric module can be adapted to transfer heat between the heat exchange chambers. The thermoelectric module may be further adapted to maintain a fluid within a predetermined temperature range in the first heat exchange chamber or the second heat exchange chamber.

Additionally or alternatively, one or more of the following features may be included in some embodiments. The thermoelectric module may regulate a therapeutic fluid within the predetermined temperature range by adding heat to or extracting heat from the temperature-regulated fluid as it flows through the first heat exchange chamber. In some embodiments the thermoelectric module mode of operation may be based upon a bi-directional Peltier-effect. The thermoelectric module may comprise a member having a first and second thermal transfer surface, and the first and second thermal transfer surface may be adapted to be thermally coupled to the first and second heat exchange chamber, respectively. The therapeutic fluid may be based, at least in part, upon a topical solution, a purified fluid solution, a sterilized fluid solution, and combinations thereof. The first heat exchange chamber may include a fluid inlet fluidly coupled to a temperature-regulated fluid source, and a fluid outlet fluidly coupled to the dressing. The second heat exchange chamber may include a second fluid inlet fluidly coupled to a second fluid source, which may be substantially the same as the temperature-regulated fluid source. The second heat exchange chamber may include a second fluid outlet fluidly coupled to a second fluid drain, which may be fluidly coupled to the temperature-regulated fluid source.

In some embodiments, the thermoelectric module may be configured to heat the fluid for a hyperthermal instillation, to cool the fluid for a hypothermal instillation, or both. Additionally or alternatively, the thermoelectric module may be a substantially tubular member with a first thermal transfer surface thermally coupled to a first heat exchange chamber and a second thermal transfer surface thermally coupled to a second heat exchange chamber. The first thermal transfer surface may be an inner surface of the substantially tubular member and the second thermal transfer surface may be an outer surface of the substantially tubular member, or vice versa. One or more of the thermal transfer surfaces may be thermally coupled to a heatsink with a plurality of heat exchange surfaces and a fan, which may be a bidirectional fan. By varying the application of power from a direct current (DC) power source to the thermoelectric module the fluid may be maintained within the predetermined temperature range. The power may be controlled by varying a voltage applied to or a current drawn by the thermoelectric module. The thermoelectric module may be alternatively configured as a thermoelectric heat source to heat the fluid in the first heat exchange chamber or as a thermoelectric cooling source to extract heat from the fluid in the first heat exchange chamber. The system may further comprise a temperature sensor, which may be inserted into the fluid proximate to a dressing or a tissue site. For example, in some embodiments, the temperature sensor may have an input for measuring temperature and an output signal indicative of the temperature.

One or more of the following features may also be included in some embodiments. The system may further comprise a controller electrically coupled to the output of the temperature sensor and the thermoelectric module. In some embodiments, for example, the controller may comprise or consist essentially of a bang-bang temperature controller configured to compare the output of the temperature sensor to a target temperature. The temperature controller may be configured to operate the thermoelectric module based on the comparison to maintain the temperature at a tissue site, as reflected by the output of the temperature sensor, within a temperature hysteresis control band, and the temperature hysteresis control band may include a maximum hysteresis temperature and a minimum hysteresis temperature. The controller may additionally or alternatively include a temperature proportional-integral-derivative (PID) controller configured to compare the measured temperature to a target temperature and vary the power applied to the thermoelectric module in response to the comparison to maintain the temperature near the target temperature. In some embodiments, the controller may be configured to periodically cycle the target temperature between a temperature minimum and a temperature maximum over a time period, which may be about 3 hours for example. The controller may reduce the temperature if the measured temperature is greater than the temperature maximum and increase the temperature if the measured temperature is less than the temperature minimum. In some embodiments, the thermoelectric module may be thermally coupled to one or more of a canister, a feed line, a bulk solutions container, a spike, a dressing, an infusion line, and a thermoelectric dressing, for example.

In other embodiments, a system for stimulating healing of tissue may comprise a negative-pressure source fluidly coupled to a dressing and adapted to maintain negative pressure at a tissue site. The system may further comprise a thermoelectric module adapted to regulate a temperature of a therapeutic fluid.

In other embodiments, a method for stimulating healing of tissue may comprise positioning a dressing at a tissue site and applying negative-pressure from a negative-pressure source to the dressing. The method may further comprise transferring heat between a first heat exchange chamber and a second heat exchange chamber using a thermoelectric module thermally coupled to the heat exchange chambers, maintaining a fluid within a predetermined temperature range, and delivering the fluid to the tissue site.

In other embodiments, a system for stimulating healing may comprise a negative-pressure source fluidly coupled to a dressing positioned at a tissue site. The system may further comprise a thermoelectric module configured to selectively heat and cool a therapeutic fluid, which is adapted to be instilled at the tissue site, and a controller coupled to the thermoelectric module and configured to provide instillation temperature-contrast therapy by alternating between the heated instilled fluid and a non-heated instilled fluid.

In some embodiments, an instillation therapy device may comprise a dressing adapted to maintain negative pressure at a tissue site and a thermoelectric module thermally coupled to, and configured to transfer heat between, a first heat exchange chamber and a second heat exchange chamber. The thermoelectric module may be further adapted to maintain a temperature-regulated fluid fluidly coupled to both the first heat exchange chamber and the dressing within a predetermined temperature range at the tissue site.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 11 is an illustrative table of test results for culture cells exposed to a temperature-contrast therapy process.

DESCRIPTION OF EXAMPLE EMBODIMENTS

Figure 1:
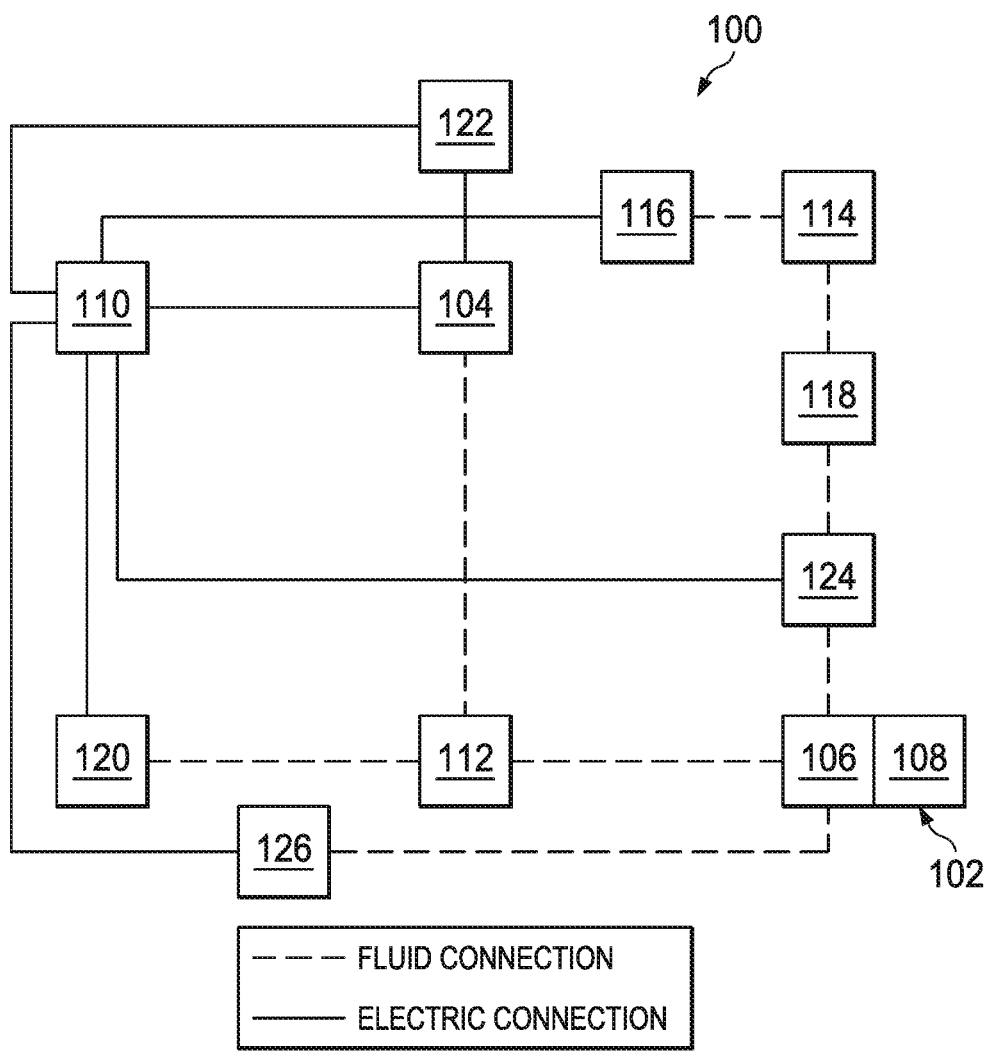
FIG. 1 is an illustrative functional block diagram of an example embodiment of a system for applying temperature-contrast therapy.

The following description of example embodiments provides information that enables a person skilled in the art to make and use the subject matter set forth in the appended claims, and may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Clinical studies and practice have shown that reducing pressure in proximity to a tissue site can augment and accelerate growth of new tissue at the tissue site. The applications of this phenomenon are numerous, and it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," and is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid to dwell for a prescribed period of time before removing the fluid. The instillation of topical treatment solutions over a wound bed can be combined with negative-pressure therapy to further promote tissue healing by loosening soluble contaminants in a wound bed and removing infectious material. For example, therapeutic fluid may be briefly instilled into the wound and allowed to diffuse or dwell for a user-specified period of time of between 10 and 20 minutes followed by between 2 and 4 hours of negative pressure at −125 mmHg. As a result, soluble bacterial burden can be decreased, contaminants removed, and the tissue cleansed.

While the clinical benefits of combining negative-pressure therapy and instillation are widely known, temperature-contrast therapy may also be an effective treatment option, and may be particularly advantageous for chronic wounds stalled in the inflammatory phase. For example, the contrasting application of warm and cold fluid, or vice versa, may shock wounds which may otherwise stall in the inflammatory phase but for the application of temperature-contrast therapy. In some embodiments, the clinical benefits of negative-pressure therapy and/or instillation may be combined with temperature-contrast therapy.

In this context, temperature-contrast therapy generally comprises a therapy or protocol where a fluid is first applied to a tissue site at a first temperature for a first interval, and is then applied to the tissue site at a second temperature for a second interval subsequent to the first interval. For example, temperature-contrast therapy may include alternating application of hypothermal fluid, hyperthermal fluid, or some combination of hypothermal and hyperthermal fluid to a tissue site for several cycles over a therapeutic period. A hypothermal fluid is a fluid having a temperature below a reference temperature, and a hyperthermal fluid is a fluid having a temperature above a reference temperature. For example, the reference temperature may be standard room temperature or body temperature. Hypothermal fluids in the range from 7 to 20, or from 4 to 24, or from 0 to 28 degrees Celsius may be particularly beneficial for some applications, and hyperthermal fluids in the range from 34 to 41, or from 32 to 43, or from 30 to 45 degrees Celsius may be particularly beneficial in some applications. In some applications, for example, the therapeutic period may be up to seven days (168 hours).

The application of the warm fluid at a tissue site may cause a widening of blood vessels and increased blood flow (vasodilation), while the application of the cold fluid may cause a constriction of blood vessels and a decrease in blood flow (vasoconstriction). The lymphatic system may also contract and relax with the alternative application of warm and cold fluids. This vacillation action may function as biological pump to dynamically circulate metabolites and replace stagnant interstitial fluid. The warm and cold fluids may be cycled within a sealed therapeutic environment provided by a dressing.

FIG. 1 is an illustrative functional block diagram of an example embodiment of a therapy system 100 for applying temperature-regulated fluid to a tissue site. In the example embodiment of FIG. 1, the therapy system 100 may also provide negative-pressure therapy, instillation therapy, or both, in addition to or combination with temperature-regulated fluid.

The term "tissue site" in this context broadly refers to the bodily tissue of any human, animal, or other organism, including bone tissue, adipose tissue, muscle tissue, neural tissue, dermal tissue, vascular tissue, connective tissue, cartilage, tendons, ligaments, or any other tissue. While tissue site may include a wound, diseased tissue, or defective tissue, the tissue site may further include healthy tissue that is not wounded, diseased, or defective. The application of temperature-regulated fluid, instillation fluid, and reduced pressure to a tissue site may be used to promote the drainage of exudate and other liquids from a tissue site, as well as promote the growth of additional tissue. In the case in which a tissue site is a wound site, the growth of granulation tissue and removal of exudates and bacteria can promote healing of the wound. The combination of temperature-controlled fluid, instillation fluid, and reduced pressure to tissue, including healthy tissue, may be used to prepare a site for tissue transplanted from another tissue location and/or to promote the growth of tissue at a site that may be harvested and transplanted to another tissue location, for example.

The therapy system 100 may include a negative-pressure supply, such as negative-pressure source 104, and may include or be configured to be coupled to a distribution component, such as a dressing 102. In general, a distribution component may refer to any complementary or ancillary component configured to be fluidly coupled to a fluid source or in a fluid path between a fluid source and a tissue site. A distribution component is preferably detachable, and may be disposable, reusable, or recyclable. For example, a dressing 102 may be fluidly coupled to a negative-pressure source 104, as illustrated in FIG. 1. A dressing 102 may include a cover 106, a tissue interface 108, or both in some embodiments. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a SENSAT.R.A.C.™ Dressing (SENSAT.R.A.C. is a trademark of KCI Licensing, Inc.). The therapy system 100 may optionally include a fluid container, such as a container 112, coupled to the dressing 102 and to the negative-pressure source 104.

The therapy system 100 may also include a source of therapeutic fluid, such as an instillation solution source, which may also be coupled to one or more distribution components. For example, fluid source 114 may be fluidly coupled to the dressing 102, as illustrated in the example embodiment of FIG. 1. The fluid source 114 may be fluidly coupled to a positive-pressure source such as the positive-pressure source 116 in some embodiments, or may be fluidly coupled to the negative-pressure source 104. A regulator, such as a fluid regulator 118, may also be fluidly coupled to the fluid source 114 and the dressing 102. In some embodiments, the regulator 118 may also be fluidly coupled to the negative-pressure source 104 through the dressing 102, as illustrated in the example of FIG. 1.

The therapy system 100 may further include a configurable fluid temperature control module, such as a thermoelectric module 124. The thermoelectric module 124 may be a heat pump and may further include a temperature sensor 126. In some embodiments, for example, the temperature sensor 126 may be a thermocouple. The thermoelectric module 124 may be fluidly coupled to the fluid source 114 and the dressing 102, as illustrated in the example embodiment of FIG. 1. The thermoelectric module 124 may be fluidly coupled to the positive-pressure source 116 in some embodiments, or may be fluidly coupled to the negative-pressure source 104. The thermoelectric module 124 may also be fluidly coupled to the positive-pressure source 116 through the regulator 118 and the fluid source 114, as illustrated in the example of FIG. 1. The thermoelectric module 124 may also be fluidly coupled to the negative-pressure source 104 through the dressing 102, as illustrated in the example of FIG. 1.

The thermoelectric module 124 may be any type of thermoelectric device driven by a stored energy, and capable of modifying the temperature of a therapeutic fluid. A non-limiting example embodiment of a thermoelectric module 124 includes a solid state thermoelectric device based upon a Peltier-effect, such as a plurality of serially connected bi-directional adapted p-n junctions. The thermoelectric module 124 may further be adapted to maintain the temperature of a fluid, which may also be an instillation solution in some embodiments, within a predetermined temperature range in response to an application of power from a DC power source.

The thermoelectric module 124 may also include or be configured to be thermally coupled to one or more heat exchange chambers and adapted to transfer heat between said heat exchange chambers. One or more heat exchange chambers may be configured to be fluidly coupled to a distribution component, such as the dressing 102.

Additionally, the therapy system 100 may include sensors to measure operating parameters and provide feedback signals to the controller 110 indicative of the operating parameters. As illustrated in FIG. 1, for example, the therapy system 100 may include one or more of a pressure sensor 120, an electric sensor 122, and a temperature sensor 126 coupled to the controller 110. The pressure sensor 120 may also be coupled or configured to be coupled to a distribution component and to the negative-pressure source 104. The temperature sensor 126 may also be coupled or configured to be coupled to a distribution component and the thermoelectric module 124. The temperature sensor 126 may be adapted to be thermally coupled to the tissue site in some embodiments. For example, the temperature sensor 126 may be inserted into the instillation solution at a location proximate to the dressing 102. The temperature sensor 126 may be adapted to have an input for sensing a tissue temperature and an output for providing a tissue temperature signal indicative of the tissue temperature to the controller 110.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A negative-pressure supply, such as the negative-pressure source 104 may be any type of manually, mechanically, or electrically operated pump. Non-limiting examples of negative-pressure source 104 include devices that are driven by stored energy, and which are capable of producing a reduced pressure. Examples of these stored energy, negative-pressure sources include, without limitation, pumps driven by primary and secondary cells, piezoelectric energy, spring energy, solar energy, kinetic energy, energy stored in capacitors, combustion, and energy developed by Sterling or similar cycles. Still other devices and processes that may be used or included in the negative-pressure source 104 include syringes, lead screws, ratchets, clockwork-driven devices, pendulum-driven devices, manual generators, osmotic processes, thermal heating processes, and processes in which vacuum pressures are generated by condensation, for example.

In some embodiments, the negative-pressure source 104 may include a pressure pump, which can provide negative pressure, i.e., a pump pressure, to the tissue site. The pressure pump may be driven by a DC motor electrically coupled to the controller 110 which is also a component of the therapy system 100.

In some embodiments, the therapy system 100 is a portable therapy system powered by a battery. The thermoelectric module 124 and pressure pump preferably use low amounts of power and are capable of operating for an extended period of time on a single charge of the battery. For example, the pressure pump may be a diaphragm pump and the electric motor may be a DC motor. The battery may be a primary cell battery, which may be a non-rechargeable lithium battery in some embodiments. Alternatively the battery may be a secondary cell battery, which may be a rechargeable lithium-ion battery pack or a rechargeable lithium polymer battery pack in some embodiments.

A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

The tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

The pathways of a manifold may be interconnected to improve distribution or collection of fluids across a tissue site. A manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. Perforated material, such as a perforated silicone, may also be suitable as a manifold in some embodiments. A manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as V.A.C. GRANUFOAM™ dressing or V.A.C. VERAFLO™ dressing, both available from Kinetic Concepts, Inc. of San Antonio, Tex. (V.A.C. GRANUFOAM and V.A.C. VERAFLO are both trademarks of KCI Licensing, Inc.).

The tissue interface 108 may be either hydrophobic or hydrophilic. A hydrophilic tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as a V.A.C. WHITEFOAM™ Dressing. (V.A.C. WHITEFOAM is a trademark of KCI Licensing, Inc.). Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

The tissue interface 108 may be constructed from bioresorbable materials. Suitable bioresorbable materials may include, without limitation, a polymeric blend of polylactic acid and polyglycolic acid. The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source 104. The cover 106 may have a high moisture-vapor transmission rate (MVTR) in some applications. For example, the MVTR may be at least 300 g/m^2 per twenty-four hours in some embodiments. The cover 106 may be a polymer drape, such as a polyurethane film, that is permeable to water vapor but impermeable to liquid, for example, such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive and having a coating weight between 25-65 grams per square meter. Thicker adhesives, or combinations of adhesives, may be applied to improve the seal and reduce leaks. Other example embodiments include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104 and/or thermoelectric module 124. For example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the power applied to the thermoelectric module 124, the pressure generated by the negative-pressure source 104, the temperature of the temperature-regulated fluid generated by the thermoelectric module 124, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120, the temperature sensor 126, or the electric sensor 122, are generally known in the art as any apparatus operable to detect or measure a physical phenomenon or property, and generally provide a signal indicative of the phenomenon or property that is detected or measured. For example, the pressure sensor 120, the temperature sensor 126, and the electric sensor 122 may be configured to measure one or more operating parameters of the therapy system 100. The pressure sensor 120 may be a transducer configured to measure pressure in a pneumatic pathway and convert the measurement to a signal indicative of the pressure measured. For example, the pressure sensor 120 may be a piezoresistive strain gauge, and the temperature sensor 126 may be a thermocouple. The electric sensor 122 may optionally measure operating parameters of the negative-pressure source 104, such as the voltage or current, in some embodiments. Preferably, the signals from the pressure sensor 120, the temperature sensor 126, and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be advantageous or required for collecting, storing, and disposing of fluids. In other environments, fluids may be properly disposed of without rigid container storage, and a re-usable container could reduce waste and costs associated with temperature-contrast therapy, negative-pressure therapy, instillation therapy, and combinations thereof.

The fluid source 114 may also be representative of a container, canister, pouch, bag, or other storage component, which can provide a therapeutic fluid for instillation therapy and/or temperature-contrast therapy, in some embodiments. Compositions of therapeutic fluid may vary according to a prescribed therapy, and may be one or more of distilled water, a topical tissue solution, a purified fluid solution, saline solution, and a sterilized fluid solution, for example. Examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment. Therapeutic fluid may be delivered from the fluid source 114 to the dressing 102, and the thermoelectric module 124 can apply or extract thermal energy from the therapeutic fluid to regulate the temperature of fluid delivered to the dressing 102. The negative-pressure source 104 may also reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

Figure 2A:
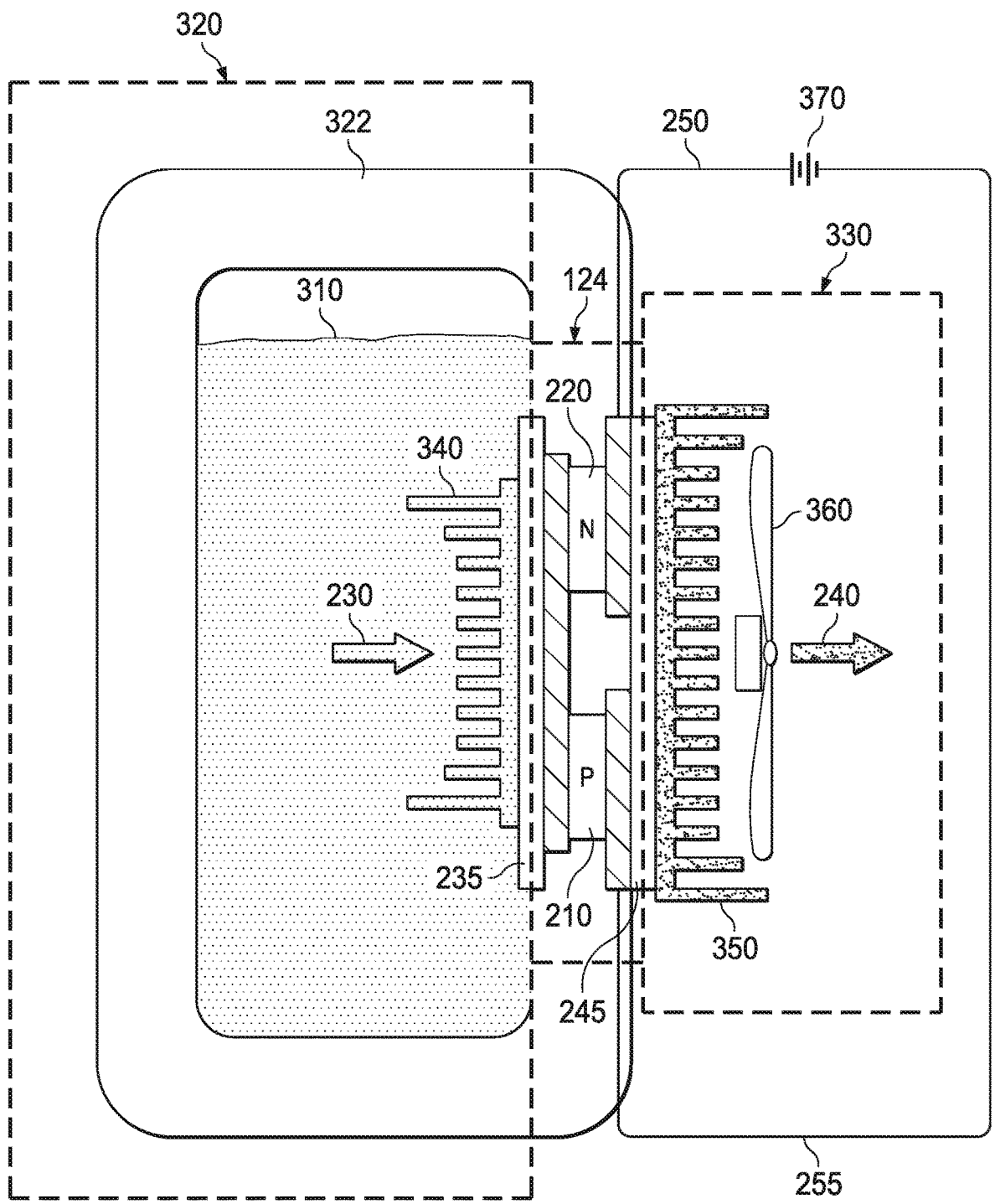
FIG. 2A is a simplified diagram illustrating a side view of an example embodiment of a thermoelectric module configured to cool a temperature-regulated fluid.

FIG. 2A is a simplified diagram illustrating additional details that may be associated with some embodiments of the thermoelectric module 124 configured to cool the fluid 310 for temperature-contrast therapy. The thermoelectric module 124 may be used to provide temperature-contrast therapy in accordance with this specification by modifying the temperature of a fluid 310, which can be delivered to a tissue site. More specifically, the thermoelectric module 124 may be adapted to regulate the fluid 310 within a predetermined temperature range.

In some embodiments, the thermoelectric module 124 may be a solid-state heat pump as depicted in FIG. 2A, and the operation of the solid-state heat pump may be based on a Peltier-effect where electrons carrying energy transfer heat across a p-n semiconductor junction. For example, heat energy may be absorbed by electrons at the (cold) p-junction as they transition from a low energy state in the p-type doped semiconductor material, such as p-type semiconductor material 210, to a high energy state in the (hot) n-type doped semiconductor material, such as n-type semiconductor material 220. Heat energy may further be expelled by electrons as they transition from a high energy state in the n-type semiconductor material 220 to a low energy state in the p-type semiconductor material 210. As illustrated in the example of FIG. 2A, the thermoelectric module 124 may comprise a first thermal transfer surface 235 and second thermal transfer surface 245.

In some embodiments, the first thermal transfer surface 235 may be configured as a cold junction to extract heat energy 230, and the second thermal transfer surface 245 may be configured as a hot junction to expel heat energy 240, as illustrated in the example embodiment of FIG. 2A. The first thermal transfer surface 235 and the second thermal transfer surface 245 may also be an electrical insulator, such as ceramic insulator, which may be a substantially flat ceramic electric insulator as illustrated in the example embodiment of FIG. 2A. The heat energy 230 may be extracted from a fluid 310 thermally coupled to the first thermal transfer surface 235, thereby cooling the fluid 310, and the expelled heat energy 240 may be expelled to a heatsink 350 thermally coupled to the second thermal transfer surface 245, thereby heating the heatsink 350.

The energy absorbed at the first thermal transfer surface 235 and pumped to the second thermal transfer surface 245 is proportional to the current passing through an individual p-n junction and a number of individual p-n junctions connected in series. Individual p-n junctions may be serially connected by a plurality of wires, which may be copper wires or the like. The serially connected p-n junctions may further be electrically coupled to conductors, such as a conductor 250 and a conductor 255 as illustrated in the example of FIG. 2A. The energy needed to create the flow of electrons may be controlled with an external power supply, such as external power supply 370, which may be electrically coupled to the conductor 250 and the conductor 255.

The Peltier-effect is a bi-directional effect and the thermoelectric module 124 may be configured to operate as a bi-directional heat pump in some embodiments. For example, continuing with the illustrative example of FIG. 2A, the thermoelectric module 124 may be configured to cool the fluid 310 thermally coupled to the first thermal transfer surface 235 if the polarity of a voltage associated with the external power supply 370 is positive, wherein the conductor 250 may be positive and the conductor 255 may be negative. Alternatively, the thermoelectric module 124 may be configured to heat the fluid 310 thermally coupled to the first thermal transfer surface 235 if the polarity of the voltage associated with the external power supply 370 is negative, wherein the conductor 250 may be the negative conductor and the conductor 255 may be the positive conductor.

The flow of electrons in a Peltier-effect thermoelectric module 124, and thereby the heat absorbed at the cold junction and pumped to the hot junction, may be controlled by varying the voltage applied to the thermoelectric module 124. The voltage applied may be varied, for example, by modulating the voltage with a square wave and varying the duty cycle of the square wave to control the heat transfer of the thermoelectric module 124. The thermoelectric module 124 may further be configured as a bi-directional solid-state heat pump. The direction of energy flow and thereby the direction of heat transfer in the bi-directional solid state heat pump may be controlled by reversing the voltage polarity of the voltage applied to the thermoelectric module 124. The power applied to the thermoelectric module 124 may alternatively or additionally be modified by varying a current drawn by the thermoelectric module 124.

The thermoelectric module 124 may be thermally coupled with a first heat exchange chamber 320 via the first thermal transfer surface 235, and the first thermal transfer surface 235 may comprise or consist essentially of a ceramic insulator in some embodiments. The first heat exchange chamber 320 may comprise or consist essentially of one or more of a fluid container, a fluid conductor, a tube, or a heatsink, for example. In the example embodiment of FIG. 2A, the first heat exchange chamber 320 includes a fluid container 322, a first heatsink 340 thermally coupled to the fluid 310, and the first thermal transfer surface 235 of the thermoelectric module 124. The first heatsink 340 in the example of FIG. 2A is configured to thermally couple the fluid 310 to the first thermal transfer surface 235 of the thermoelectric module 124. In the example embodiment of FIG. 2A the first heatsink 340 includes a plurality of heat exchange surfaces or fins to maximize the surface area of first heatsink 340 in contact with the fluid 310 and thereby maximize the heat energy 230 extracted from the fluid 310.

Continuing with the illustrative example of FIG. 2A, the thermoelectric module 124 may also be thermally coupled with a second heat exchange chamber 330 via a second thermal transfer surface 245, and the second thermal transfer surface 245 may be a ceramic insulator in some embodiments. The second heat exchange chamber 330 may comprise or consist essentially of one or more of a fluid container, a fluid conductor, a tube, or a heatsink, for example. In the example embodiment of FIG. 2A, the second heat exchange chamber 330 includes the second heatsink 350, a fan 360, and the second thermal transfer surface 245 of the thermoelectric module 124. The second heatsink 350 may include a plurality of heat exchange surfaces or fins as disclosed above. Heat energy 240 may be expelled from the surface of the second heatsink 350 with the aid of the fan 360, which may be configured to draw air over the fins of the second heatsink 350. In some embodiments, the fluid 310 may also be used as a thermal mass (heatsink) in the second heat exchange chamber 330. By expelling heat energy 240 from the hot side of the thermoelectric module 124, a temperature differential is maintained across thermoelectric module 124, which otherwise would quickly reach stasis and do nothing.

In FIG. 2A, the positive conductor 250 is connected to the n-type semiconductor material 220 and the negative conductor 255 is connected to the p-type semiconductor material 210. The material of the conductor 250 and the conductor 255 may include one or more of copper, silver, and gold, for example. The fluid 310 is thermally coupled to the first thermal transfer surface 235 in the example of FIG. 2A, and the thermoelectric module 124 is configured to cool the temperature-regulated if the polarity of a voltage associated with an external power supply 370 is positive.

In other embodiments, FIG. 2A may alternatively depict the cross-section of a longitudinal tube through which the fluid 310 may flow perpendicular to the plane of FIG. 2A, rather than a container 322 to retain the fluid 310. The first heat exchange chamber 320 may be fluidly coupled to a fluid inlet and a fluid outlet. The fluid inlet may be fluidly coupled to a fluid source, which may be a fluid container. The fluid outlet may be fluidly coupled to the dressing 102, which may include a cover 106, a tissue interface 108, or both in some embodiments.

Figure 2B:
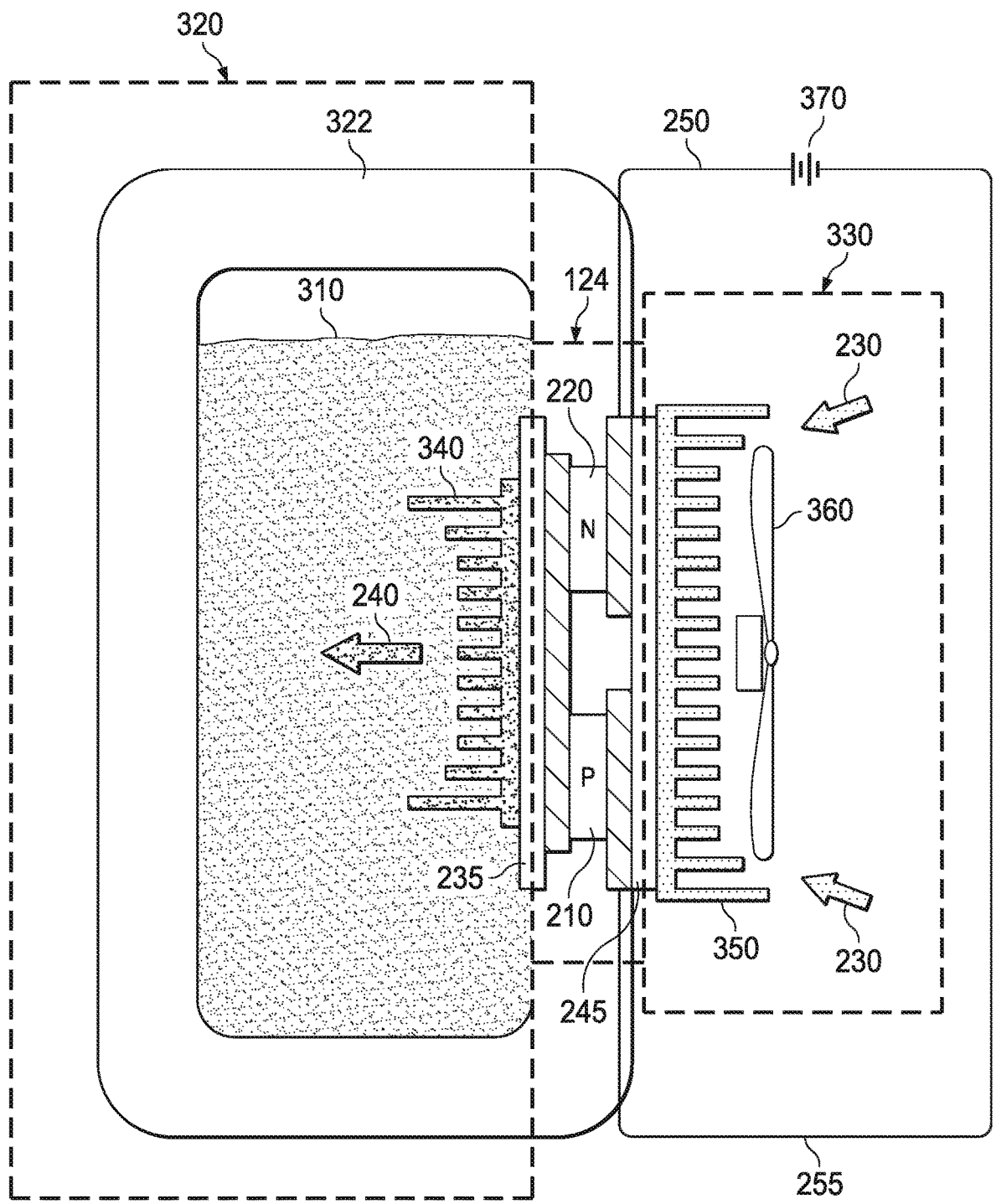
FIG. 2B is a simplified diagram illustrating a side view of an example embodiment of a thermoelectric module configured to heat a temperature-regulated fluid.

FIG. 2B is a simplified diagram illustrating additional details that may be associated with some embodiments of the thermoelectric module 124 configured to heat the fluid 310 for temperature-contrast therapy. The thermoelectric module 124 may be thermally coupled with a first heat exchange chamber 320 via a first thermal transfer surface 235, and the first thermal transfer surface 235 may comprise or consist essentially of a ceramic insulator in some embodiments. The first heat exchange chamber 320 may be one or more of a fluid container, a fluid conductor, a tube, or a heatsink for example. In the example embodiment of FIG. 2B the first heat exchange chamber 320 includes a fluid container 322, a first heatsink 340 thermally coupled to the fluid 310, and a first thermal transfer surface 235 of the thermoelectric module 124.

Continuing with the illustrative example from above, the thermoelectric module 124 may also be thermally coupled with a second heat exchange chamber 330 via a second thermal transfer surface 245, and the second thermal transfer surface 245 may be a ceramic insulator in some embodiments. The second heat exchange chamber 330 may comprise or consist essentially of one or more of a fluid container, a fluid conductor, a tube, or a heatsink, for example. In the example embodiment of FIG. 2B, the second heat exchange chamber 330 includes a second heatsink 350, a fan 360, and a second thermal transfer surface 245 of the thermoelectric module 124. The second heatsink 350 may include a plurality of heat exchange surfaces or fins. Heat energy 230 may be extracted from the air with the aid of the fan 360, which may be configured to blow air over the fins of the second heatsink 350.

In the illustrative example of FIG. 2B, the fluid 310 is thermally coupled to the first thermal transfer surface 235, and the thermoelectric module 124 is configured to heat the fluid 310 if the polarity of a voltage associated with the external power supply 370 is negative. In this configuration the negative conductor 255 is connected to the n-type semiconductor material 220, and the positive conductor 250 is connected to the p-type semiconductor material 210.

By changing the polarity of the voltage applied to the fan 360 and thereby the direction of rotation of the fan 360, the fan 360 may be configured to either draw or blow air over the second heatsink 350. The polarity of the voltage applied to the fan 360 and the polarity of the voltage applied to the thermoelectric module 214 may be synchronized in some embodiments.

In other embodiments, the fan 360 may be omitted and the second heat exchange chamber 330 may instead be adapted to allow a second fluid to flow through the second heat exchange chamber 330 perpendicular to the plane of FIG. 2B. The second heat exchange chamber 330 may include a second fluid inlet, and the second fluid inlet may be fluidly coupled to a second fluid source, which may be a second fluid container. Alternatively, the second fluid inlet may be coupled to the fluid source 114 in some embodiments.

Figure 3A:
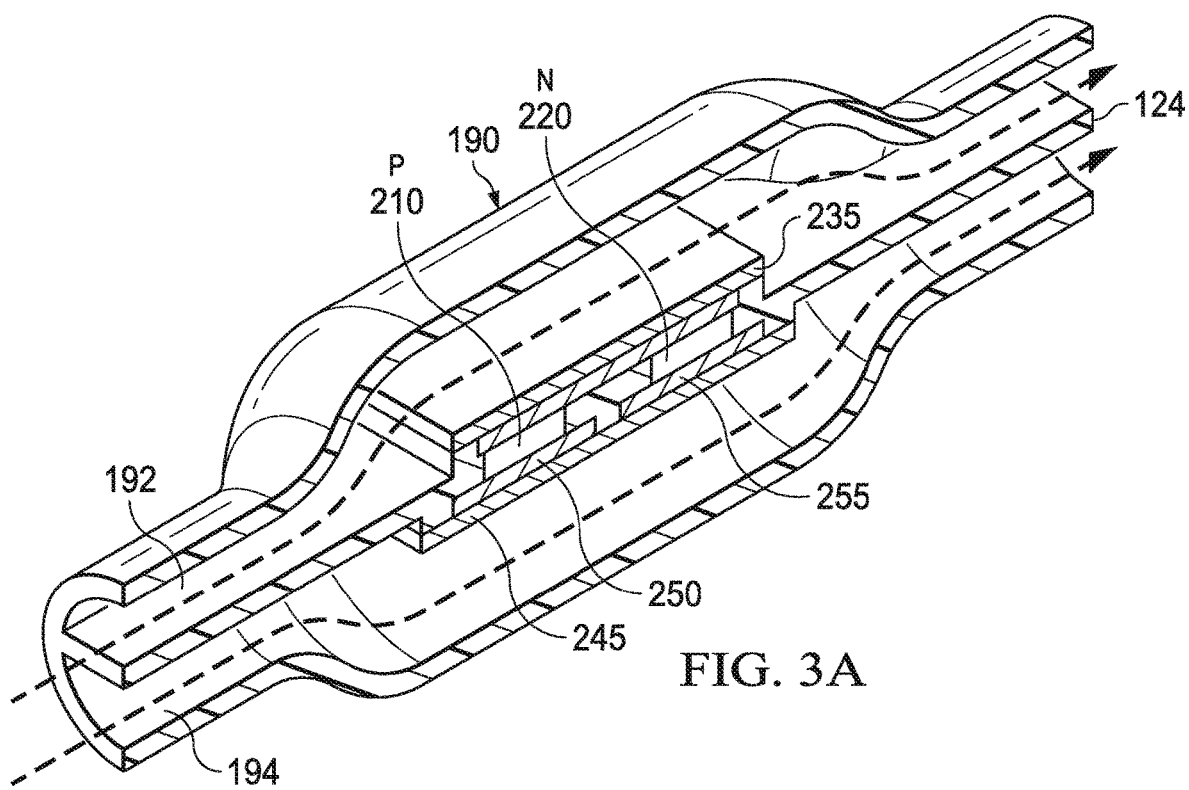
FIGS. 3A-3B are perspective views of example embodiments of multi-lumen tubes that may be associated with some embodiments of the system of FIG. 1.

FIG. 3A is a perspective view of a multi-lumen tube 190, which may be associated with some embodiments of the therapy system 100. The tube 190 generally comprises a first lumen 192 and a second lumen 194. In some example embodiments, the fluid 310 may flow from the fluid source 114 through the lumen 192. The lumen 192 may be fluidly coupled to a heat exchange chamber, such as the first heat exchange chamber 320, where the temperature-regulated fluid may be alternatively heated or cooled, and to the dressing 102.

The second lumen 194 may be fluidly coupled to a second heat exchange chamber, such as the second heat exchange chamber 330. The second heat exchange chamber 330 may be fluidly coupled to a fluid, which may be alternatively heated or cooled by the second heat exchange chamber 330. The fluid may flow through the second heat exchange chamber 330, in some embodiments. For example, the fluid may flow from a source, which may be the fluid source 114, through the second lumen 194 and the second heat exchange chamber 330 and then to a container for collection, which may be container 112. Alternatively, the fluid may be recirculated back to the fluid source. The fluid, circulating or otherwise, may act as a thermal mass or heatsink for the thermoelectric module 124. Alternatively or additionally, the second heat exchange chamber 330 may be a heatsink or may be coupled to a heatsink, in some embodiments.

Figure 3D:
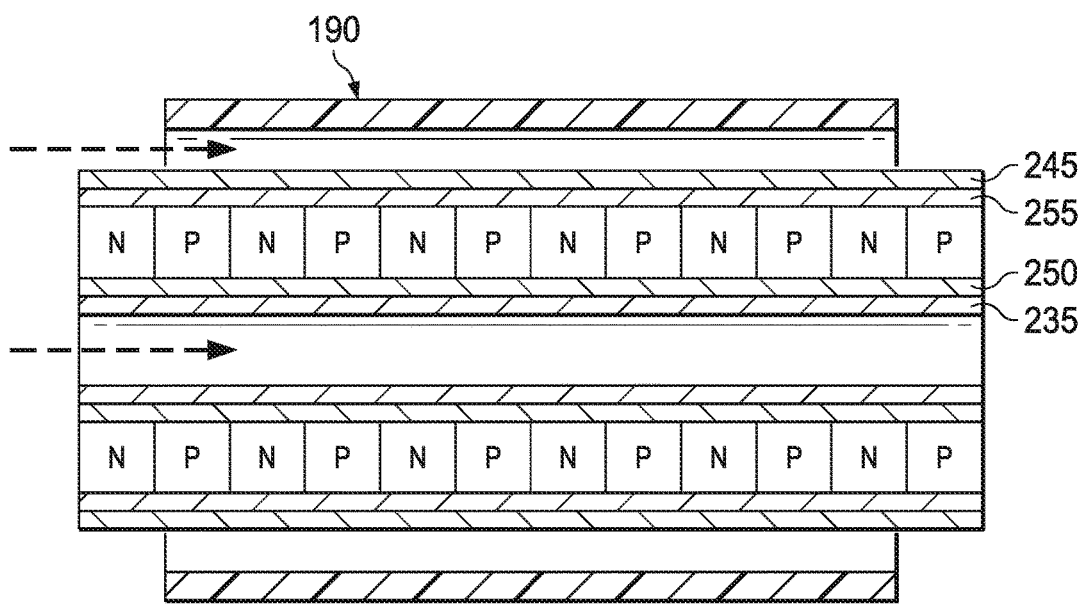
FIGS. 3C-3D are sectional views of the multi-lumen tube depicted in the example embodiment of FIG. 3B.
Figure 3B:
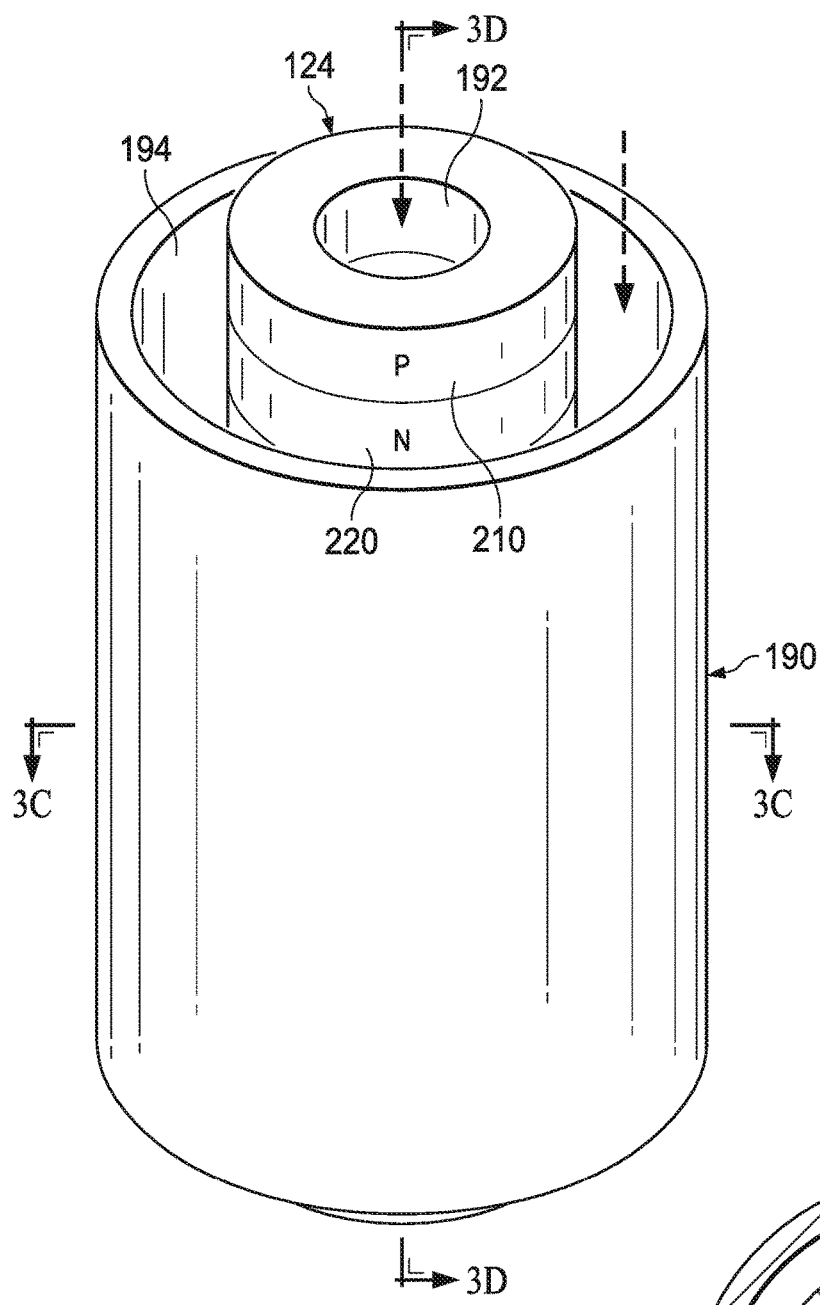
Figure 3C:
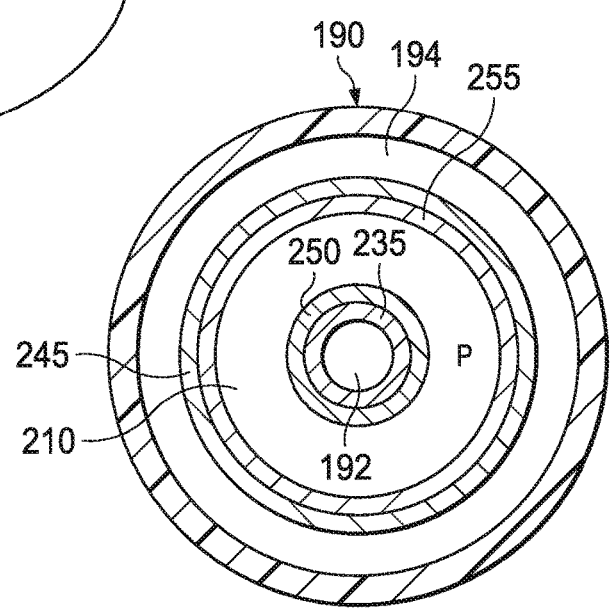

The thermoelectric module 124 may be configured to be a part of the multi-lumen tube 190 in some embodiments. For example, the thermoelectric module 124 may, in part, partition the multi-lumen tube 190, and therefore the first and second heat exchange chambers 320, 330, as depicted in the embodiment of FIG. 3A. In other embodiments, the thermoelectric module 124 may be a substantially tubular member having a plurality of alternately arranged p-type doped semiconductor material and n-type doped semiconductor material formed essentially in a ring shape, as illustrated in FIG. 3B. For example, a p-type doped semiconductor ring 210 and an n-type doped semiconductor ring 220 may be connected electrically to one another to form an individual p-n junction and a number of individual p-n junctions may be serially connected. The tubular member may have a first thermal transfer surface 235 thermally coupled to a first heat exchange chamber 320 and a second thermal transfer surface 245 thermally coupled to a second heat exchange chamber 245. The first thermal transfer surface 235 may be an inner surface of the substantially tubular member and the second thermal transfer surface 245 may be an outer surface of the substantially tubular member, or vice versa. The first thermal transfer surface 235 and/or second thermal transfer surface 245 may comprise or consist essentially of a ceramic insulator in some embodiments. The tubular member may further be encapsulated by a tube, thereby forming a multi-lumen tube 190 with an inner lumen 192 and an outer lumen 194. FIG. 3C is a horizontal sectional view of the multi-lumen tube depicted in the example embodiment of FIG. 3B. The cutting plane of FIG. 3C intersects one of the p-type doped semiconductor rings 210 and shows the interior construction of the tubular thermoelectric module 124. Specifically, FIG. 3C depicts concentric circles corresponding to an encapsulating tube of the multi-lumen tube 190, an outer lumen 194, a second thermal transfer surface 245, an outer conductor 245, a p-type doped semiconductor ring 210, a first thermal transfer surface 235, an inner conductor 250, and an inner lumen 192. FIG. 3D is a corresponding vertical sectional view of the multi-lumen tube depicted in the example embodiment of FIG. 3B. In FIG. 3D the cutting plane shows the interior construction of the tubular thermoelectric module 124 along its longitudinal length. Specifically, FIG. 3D depicts the alternately arranged p-type doped semiconductor rings 210 and n-type doped semiconductor rings 220 within the body of tubular thermoelectric module 124.

In some embodiments, fluid may flow from a source such as the fluid source 114 through one lumen, such as the lumen 192 of the multi-lumen tube 190, and to the dressing 102. The fluid 310 may be alternatively heated or cooled within the first heat exchange chamber of the thermoelectric module 124. The outer lumen 194 may be fluidly coupled to a fluid, which may flow through the second heat exchange chamber 330 of the thermoelectric module 124 and act as a thermal mass (heatsink) for the thermoelectric module 124.

Figure 4:
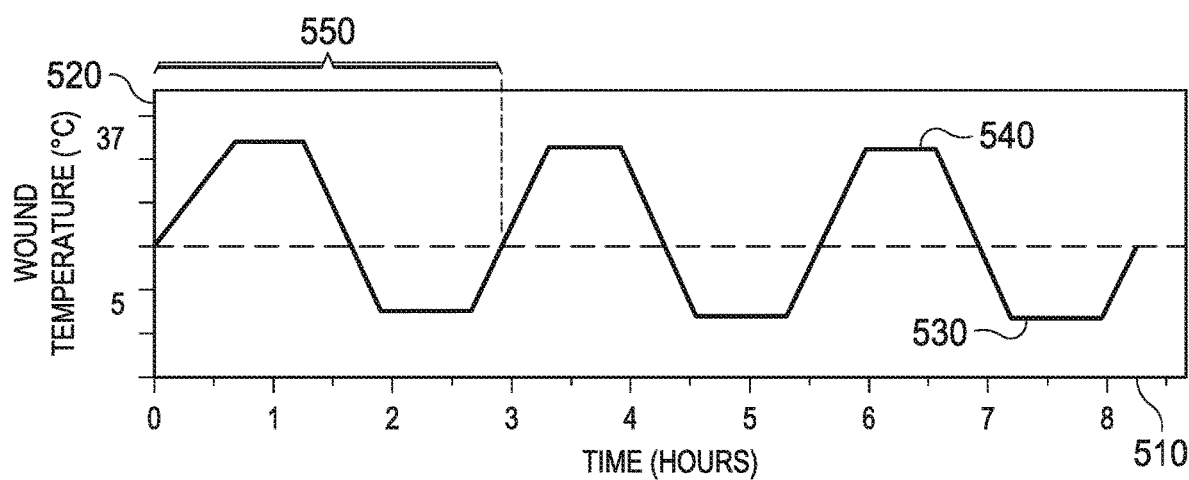
FIG. 4 is a graph of temperature regulation of a temperature-regulated fluid in accordance with an example embodiment, the x-axis representing time in hours and the y-axis representing temperature of a fluid as regulated by a thermoelectric module.

FIG. 4 is a graph illustrating additional details that may be associated with temperature control of some embodiments of the thermoelectric module 124. In FIG. 4, the x-axis 510 represents time in hours and the y-axis 520 represents temperature of a regulated fluid in degrees Celsius (° C.) as regulated by the thermoelectric module 124. The temperature regulation may be determined based on, at least in part, a controller 110 that compares a manipulated variable, such as a temperature at a tissue site measured by the temperature sensor 126, to a target temperature and a control variable. The control variable may be based upon, at least in part, the application of power from a DC power source to the thermoelectric module 124 by the controller 110 in some embodiments.

In some embodiments, the control variable may be based upon, at least in part, a modification of a flow rate of fluid 310 from the fluid source 114 to the dressing 102. The flow rate may be modified by an application of power from the DC power source to the positive-pressure source 116 by the controller 110. Additionally or alternatively, the flow rate may be modified by an application of power from the DC power source to the negative-pressure source 104 by the controller 110. The flow rate may also be regulated by the regulator 118. While the flow rate may vary based upon, at least in part, feedback from the temperature sensor 126, the flow of fluid 310 may be substantially continuous for the duration of the therapeutic cycle in some embodiments. Alternatively, the flow of fluid 310 may be intermittent or periodic. For example, the flow of fluid 310 may occur at intervals determined based upon, at least in part, input from an operator or in response to feedback from the temperature sensor 126.

In some embodiments, the controller 110 may be coupled to the output of the temperature sensor 126 and the thermoelectric module 124, and may include a hysteresis temperature controller that compares the output temperature to a target temperature and maintains the output temperature within a temperature hysteresis control band. The temperature hysteresis control band may include a maximum hysteresis temperature and a minimum hysteresis temperature. The controller 110 may additionally or alternatively include a temperature proportional-integral-derivative (PID) controller that compares the output temperature to a target temperature and varies the power applied to the thermoelectric module 124 in response to the comparison to maintain the output temperature near the target temperature. The controller 110 may reduce the temperature at the tissue site if the output temperature is greater than the temperature maximum 540 and increase the temperature at the tissue site if tissue temperature is less than the temperature minimum 530.

In some embodiments, the controller 110 may be configured to periodically cycle the tissue temperature between the temperature minimum 530 and the temperature maximum 540 over a predetermined therapeutic time period 550. For example, the temperature at the tissue site may be cycled over a 3 hour time period and the tissue site temperature may be cycled one or more times during a therapeutic life cycle. While the amount and nature of the temperature-contrast therapy applied to the tissue site may vary according to therapeutic requirements, the temperature maximum 540 may be a temperature between 34° C. and 41° C. and the temperature minimum 530 may be a temperature between 4° C. and 20° C., in some embodiments. More specifically the temperature maximum 540 may be about 37° C. and the temperature minimum 530 may be about 5° C., in some embodiments. The controller 110 may further be configured to maintain the temperature minimum 530 and/or temperature maximum 540 for a fixed period of time, for example, between 1 and 30 minutes, in some embodiments.

In some embodiments, the controller 110 may be configured to periodically cycle the tissue temperature between the temperature maximum 540 and the temperature minimum 530, and the temperature minimum 530 may correspond to a non-heated fluid or the temperature of the surrounding environment or the ambient temperature.

The thermoelectric module 124 may be configured to transfer heat energy 240 to the fluid 310 in the fluid source 114. Additionally or alternatively the thermoelectric module 124 may be configured to extract heat energy 230 from the fluid 310 in the fluid source 114.

Figure 5:
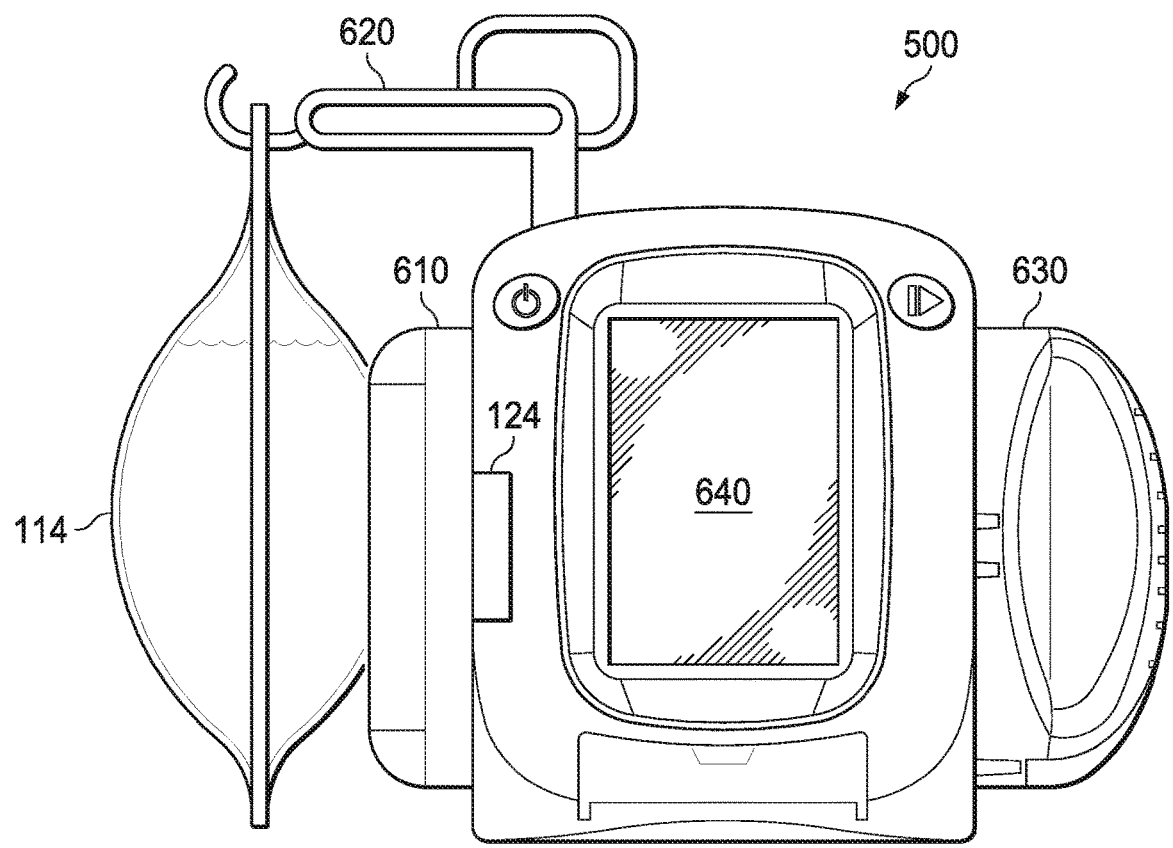
FIG. 5 is front view of a therapy unit illustrating additional details that may be associated with some embodiments of the system of FIG. 1.

FIG. 5 is a front view of a therapy unit 500, illustrating additional details that may be associated with some example embodiments of the therapy system 100. The therapy unit 500 of FIG. 5 is generally configured for instillation therapy and negative-pressure therapy. The therapy unit 500 may include a thermoelectric module 124 thermally coupled to the fluid source 114, thereby enabling the combined system to be configured for contrast therapy in some embodiments. A fluid adapter 610, which may be an instillation cassette, for example, may be coupled to one side of the therapy unit 500. The therapy unit 500 of FIG. 5 may also include a solution container hanger arm 620. FIG. 5 also illustrates an example embodiment of the container 112 coupled to a side of the therapy unit 500. The therapy unit 500 may also include a display or other operator interface, such as display 640, which operator may use to configure and monitor the temperature-contrast therapy.

As illustrated in the embodiment of FIG. 5, the thermoelectric module 124 may be partially or fully encapsulated within a wall proximate to the adapter 610 in some embodiments. The thermoelectric module 124 may be configured to transfer heat energy 240 to the fluid 310 contained by the fluid source 114. Additionally or alternatively, the thermoelectric module 124 may be configured to extract heat energy 230 from the fluid 310 contained by the fluid source 114.

In some embodiments, the thermoelectric module 124 may be inserted in-line with an infusion line (not shown). The thermoelectric module 124 may be configured to transfer heat energy 240 to the fluid 310 in the infusion line. Additionally or alternatively, the thermoelectric module 124 may be configured to extract heat energy 230 from the fluid 310 in the infusion line.

In some embodiments, the thermoelectric module 124 and/or a thermocouple may be configured to be integrated into the dressing 102, and the dressing 102 may be applied directly to the tissue site. The dressing 102 may include a cover 106, a tissue interface 108, or both.

Figure 6:
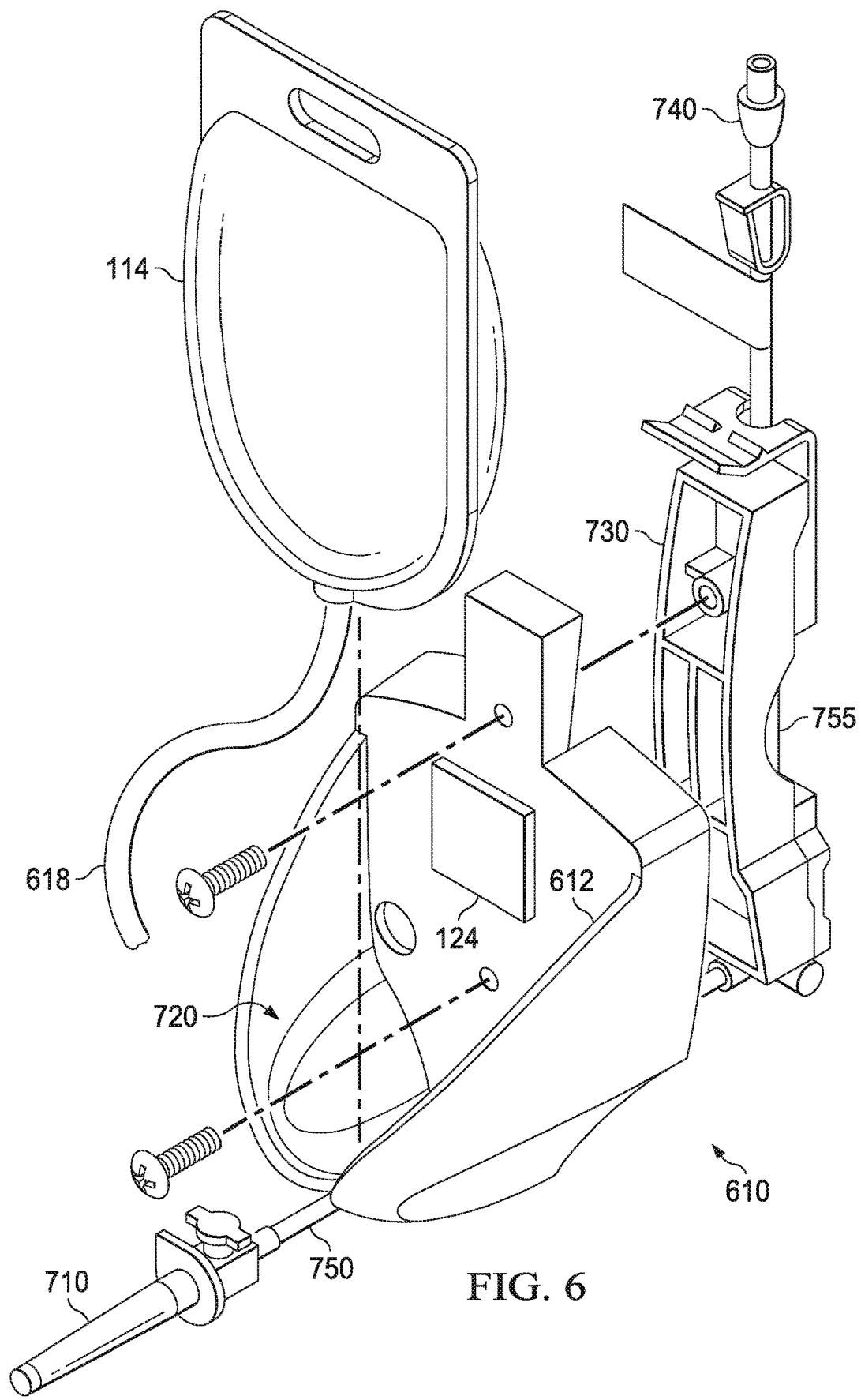
FIG. 6 is a schematic diagram of fluid adapter illustrating additional details that may be associated with some embodiments of the therapy unit of FIG. 5.

FIG. 6 is a schematic diagram illustrating additional details that may be associated with other embodiments of the therapy unit 500. For example, the thermoelectric module 124 may be coupled to a wall 612 of a receptacle 720 in the adapter 610. The adapter 610 of FIG. 6 may include a tubing spike 710 and a receptacle 720 for the fluid source 114. In the example of FIG. 6, the fluid source 114 comprises a bulk container for a therapeutic fluid. The adapter 610 of FIG. 6 may also include a mounting bracket, such as a mounting bracket 730, in some embodiments. The receptacle 720 may be mechanically coupled to the mounting bracket 730. The adapter 610 of FIG. 6 may also include a feed line connector, such as a connector 740. The connector 740 may be fluidly coupled to the fluid source 114 via an interconnecting tube, such as interconnecting tube 618. The tubing spike 710, the connector 740 and/or the fluid source 114 may be fluidly coupled to each other to provide a path for transferring fluid 310 in some embodiments. For example, the connector 740 and the tubing spike 710 may be fluidly coupled through one or more feed lines, such as a feed lines 750 and 755. In some embodiments, one or more of the feed line 750 and 755 may be integrated into the receptacle 720.

Figure 7A:
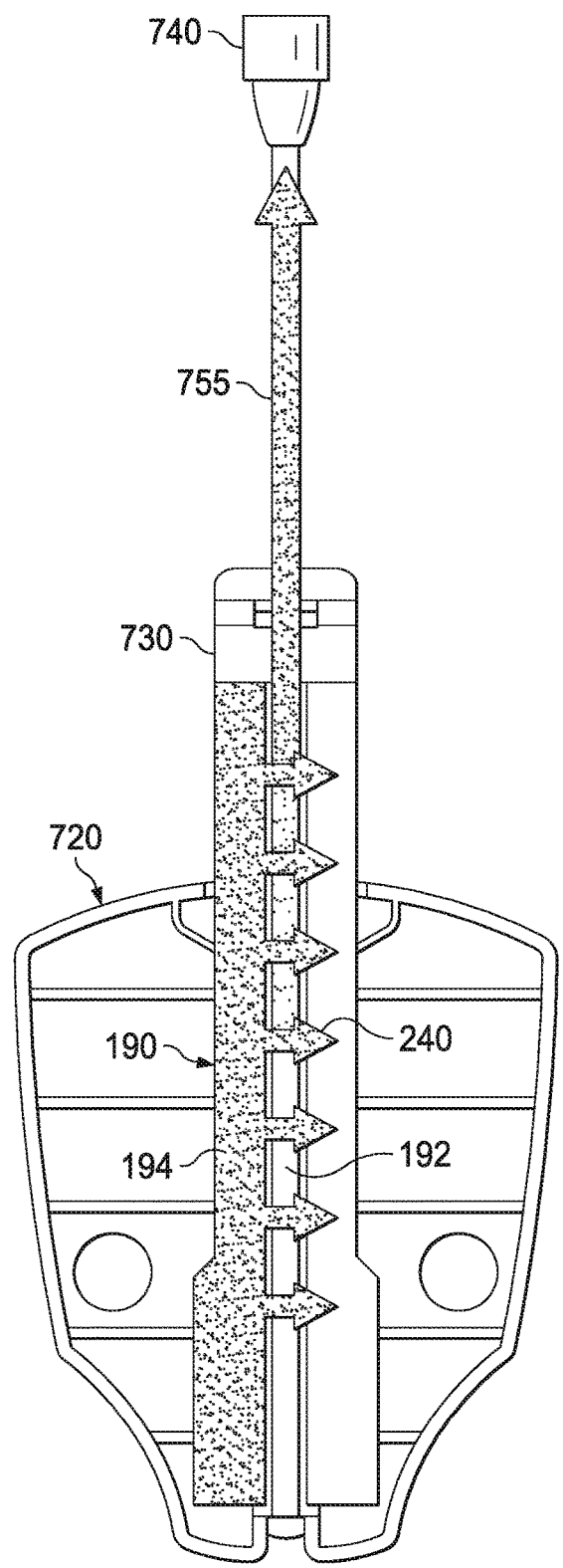
FIG. 7A is a diagram of an example embodiment of a combined mounting bracket and receptacle configured to heat a temperature-regulated fluid in the system of FIG. 1.
Figure 7B:
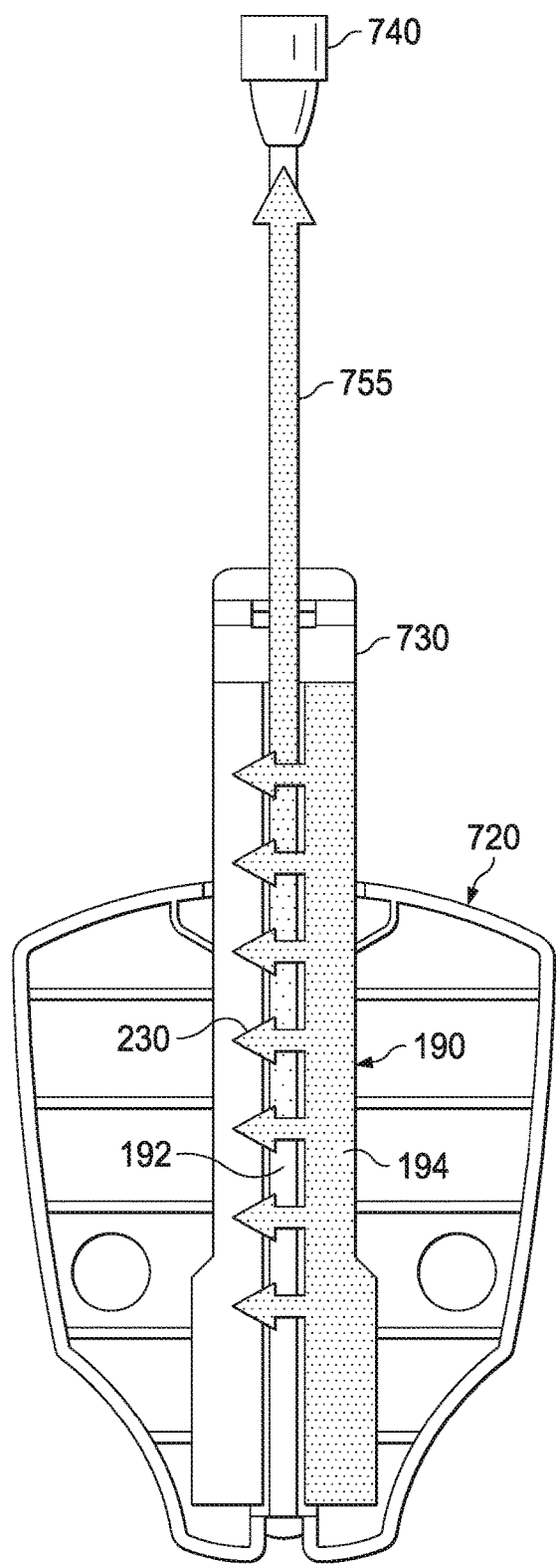
FIG. 7B is a diagram of an example embodiment of a combined mounting bracket and receptacle configured to cool a temperature-regulated fluid in the system of FIG. 1.

FIG. 7A and FIG. 7B are diagrams illustrating additional details that may be associated with some example embodiments of the therapy unit 500. In some embodiments, the thermoelectric module 124 may be thermally coupled to a feed line 755 of the adapter 610. For example, the thermoelectric module 124 may be inserted into or attached to the feed line 755. The thermoelectric module 124 may be configured to transfer heat energy to the fluid 310 flowing through the feed line 755; additionally or alternatively, the thermoelectric module 124 may be configured to extract heat energy 230 from the fluid 310 flowing through the feed line 755. In the example of FIG. 7A, the thermoelectric module 124 is configured to transfer heat energy 240 to the fluid 310 in the feed line 755, and in the example of FIG. 7B, the thermoelectric module 124 is configured to extract heat energy 230 from the fluid 310 in the feed line 755.

Figure 8A:
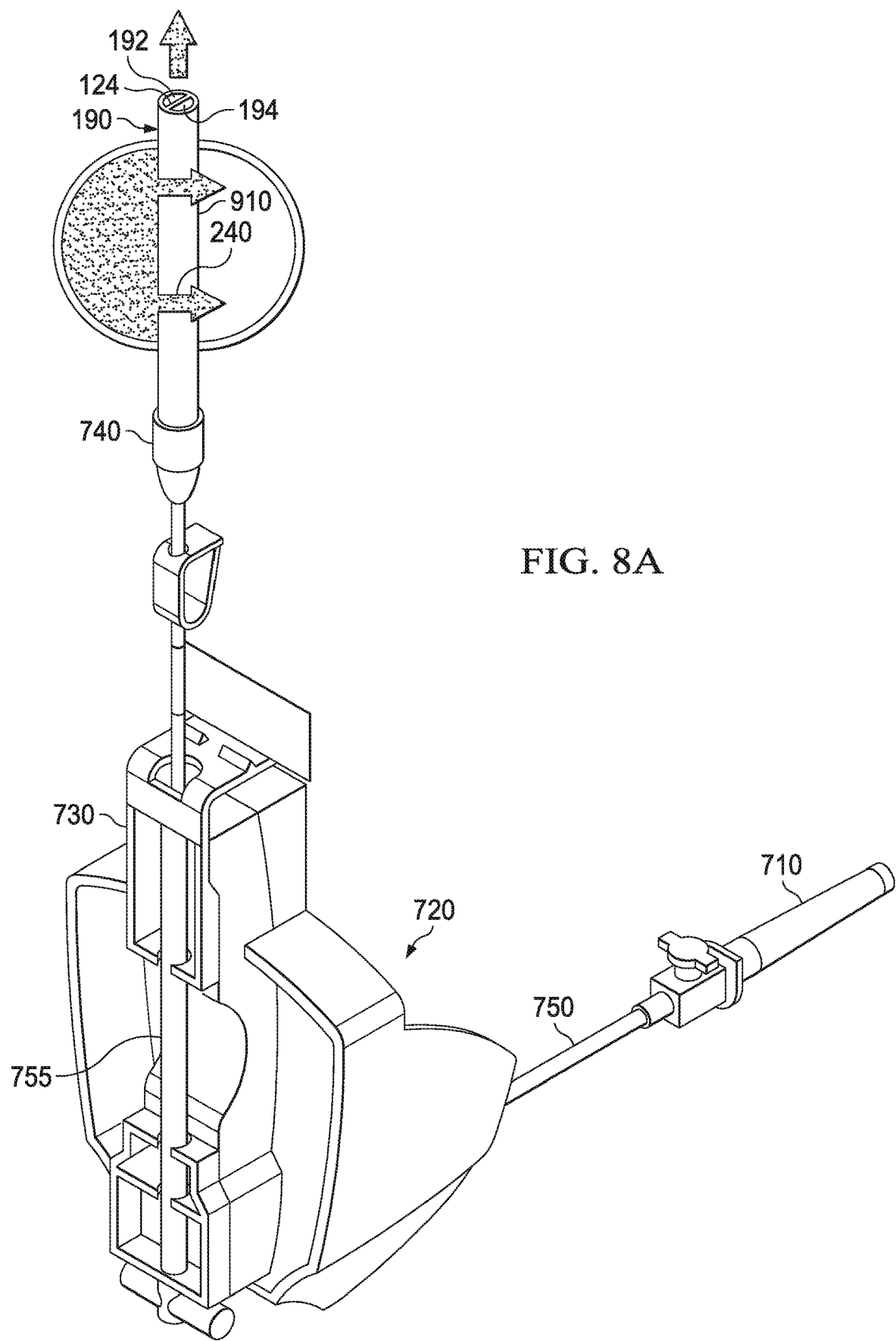
FIGS. 8A-8B are perspective views of example embodiments of tubing feed lines that may be associated with some embodiments of the system of FIG. 1.
Figure 8B:
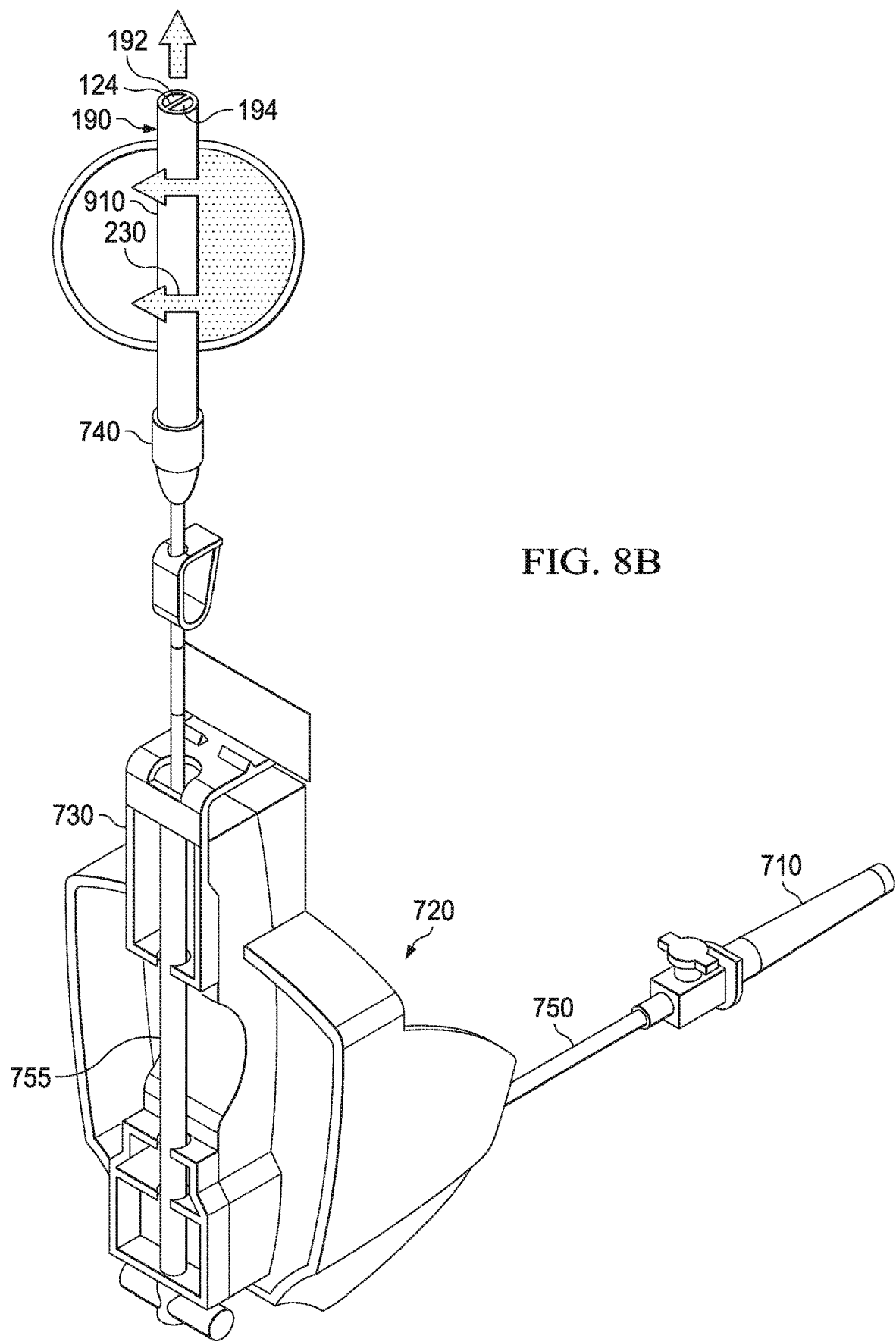

FIG. 8A and FIG. 8B are diagrams illustrating details that may be associated with some embodiments of the therapy unit 500. As illustrated in the embodiment of FIG. 8A and FIG. 8B, the thermoelectric module 124 may be thermally coupled to a tubing feed line 910. For example, the thermoelectric module 124 may be inserted into a tubing feed line 910 in some embodiments. The thermoelectric module 124 may be configured to transfer heat energy 240 to the fluid 310 flowing through the tubing feed line 910; additionally or alternatively the thermoelectric module 124 may be configured to extract heat energy 230 from the fluid 310 in the tubing feed line 910. In the example of FIG. 8A, the thermoelectric module 124 is configured to transfer heat energy 240 to the fluid 310 in the tubing feed line 910. In the example of FIG. 8B, the thermoelectric module 124 has been configured to extract heat energy 230 from the fluid 310 in the tubing feed line 910.

Figure 9A:
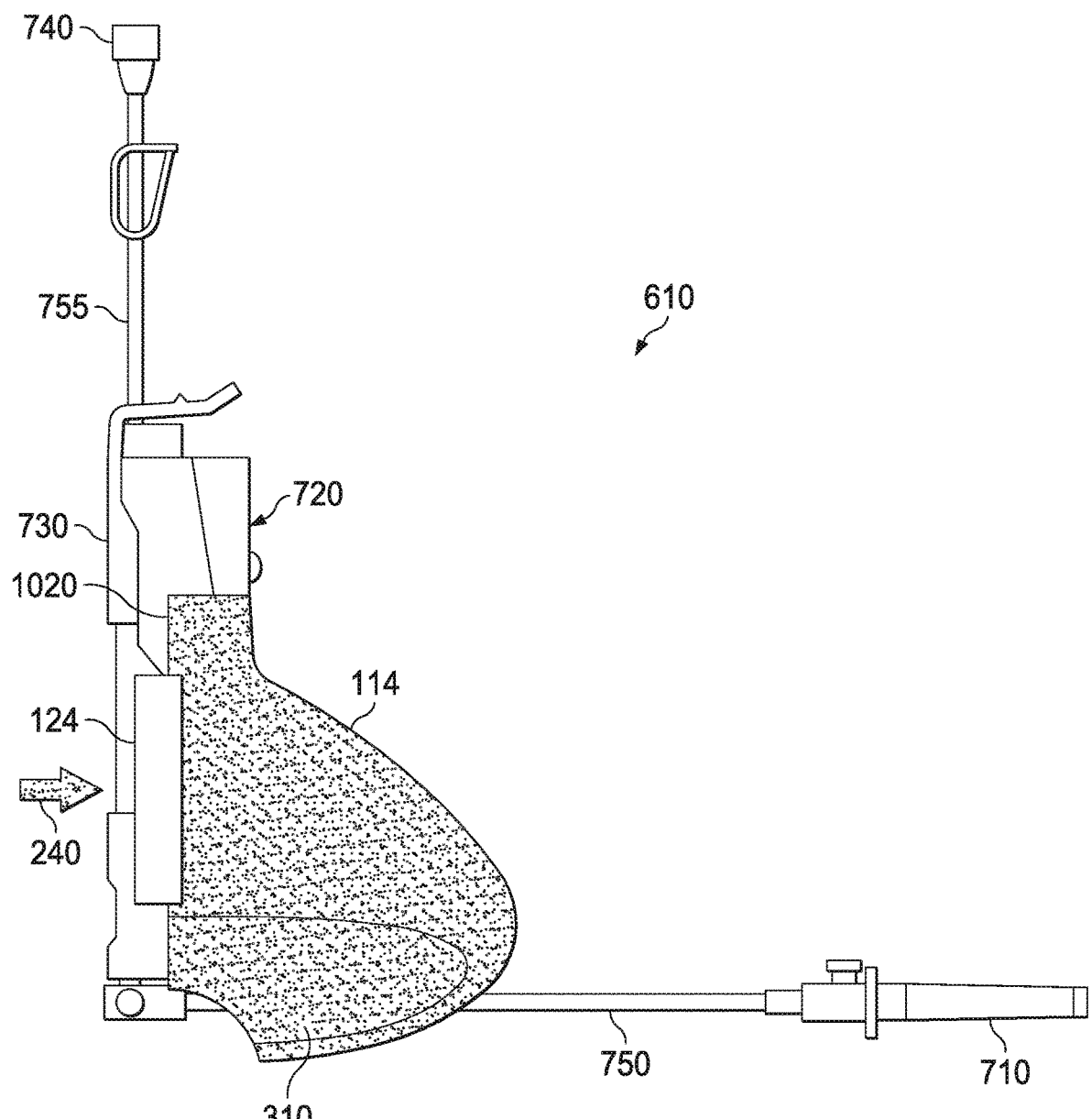
FIG. 9A-9B are side views diagrams of example embodiments of bulk solution containers that may be associated with some embodiments of the system of FIG. 1.
Figure 9B:
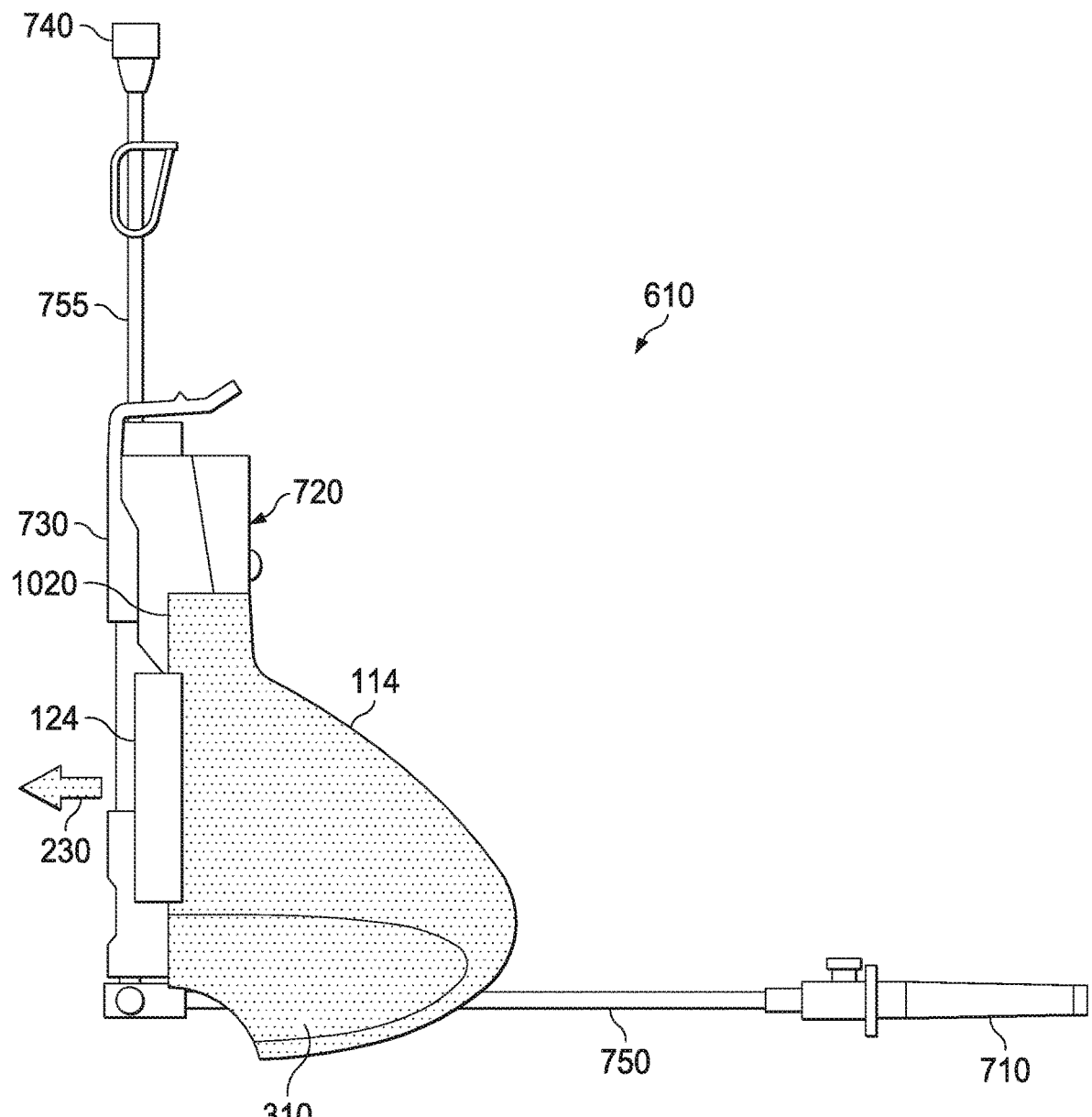

FIG. 9A and FIG. 9B are diagrams illustrating additional details that may be associated with some embodiments of the therapy unit 500. As illustrated in the embodiment of FIG. 9A and FIG. 9B, the thermoelectric module 124 may be thermally coupled to the fluid source 114, which may be a bulk solution container. For example, the thermoelectric module 124 may be partially or fully encapsulated within a wall 1020 of the adapter 610 in some embodiments. The thermoelectric module 124 may be configured to transfer heat energy 240 to a fluid 310 contained in the fluid source 114. Additionally or alternatively the thermoelectric module 124 may be configured to extract heat energy 230 from the fluid 310 contained in the fluid source 114. In the example of FIG. 9A, the thermoelectric module 124 is configured to transfer heat energy 240 to the fluid 310, and in the example of FIG. 9B the thermoelectric module 124 is configured to extract heat energy 230 from the fluid 310.

Figure 10A:
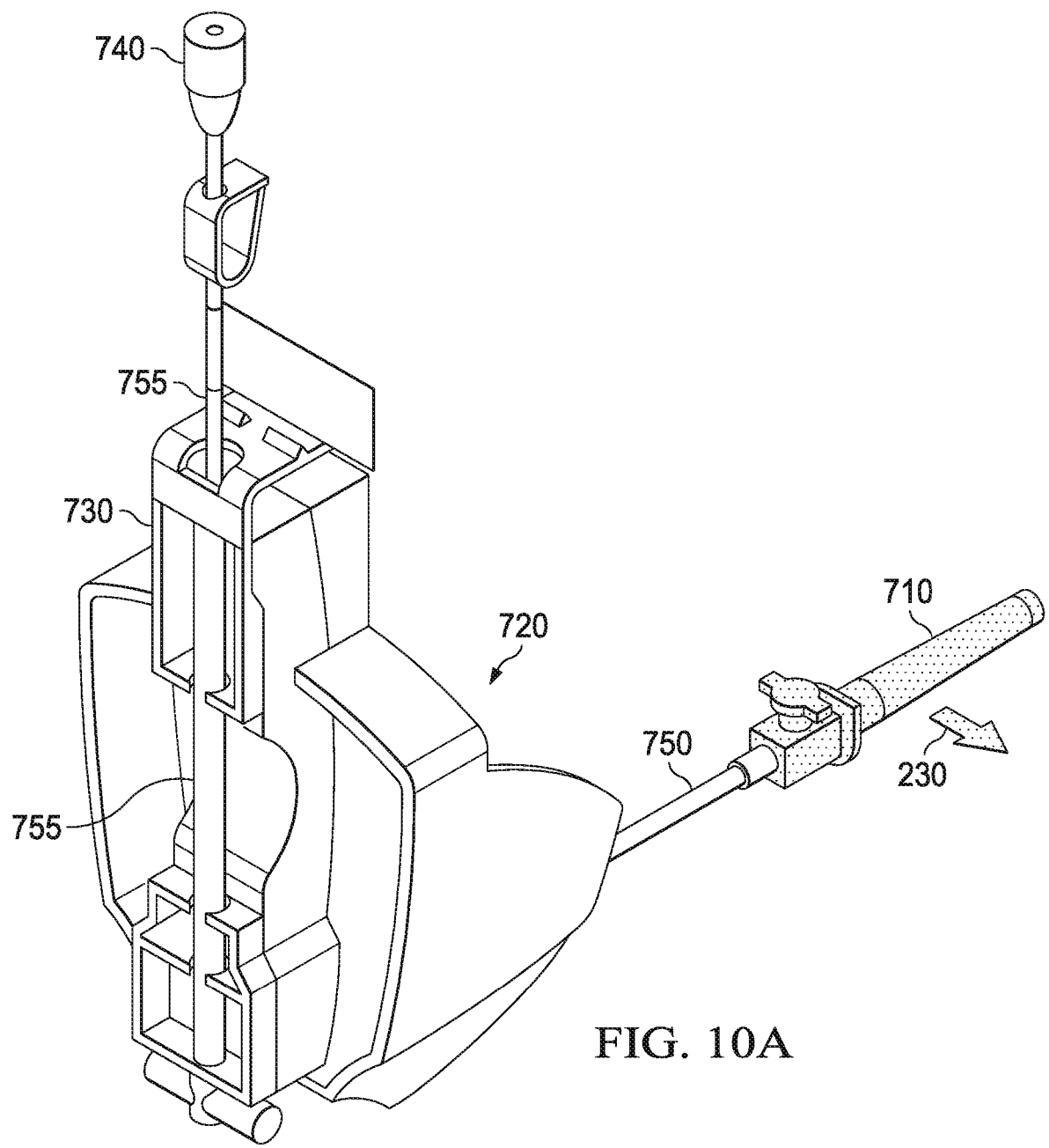
FIGS. 10A-10B, are perspective views of example embodiments of tubing spikes that may be associated with some embodiments of the system of FIG. 1.
Figure 10B:
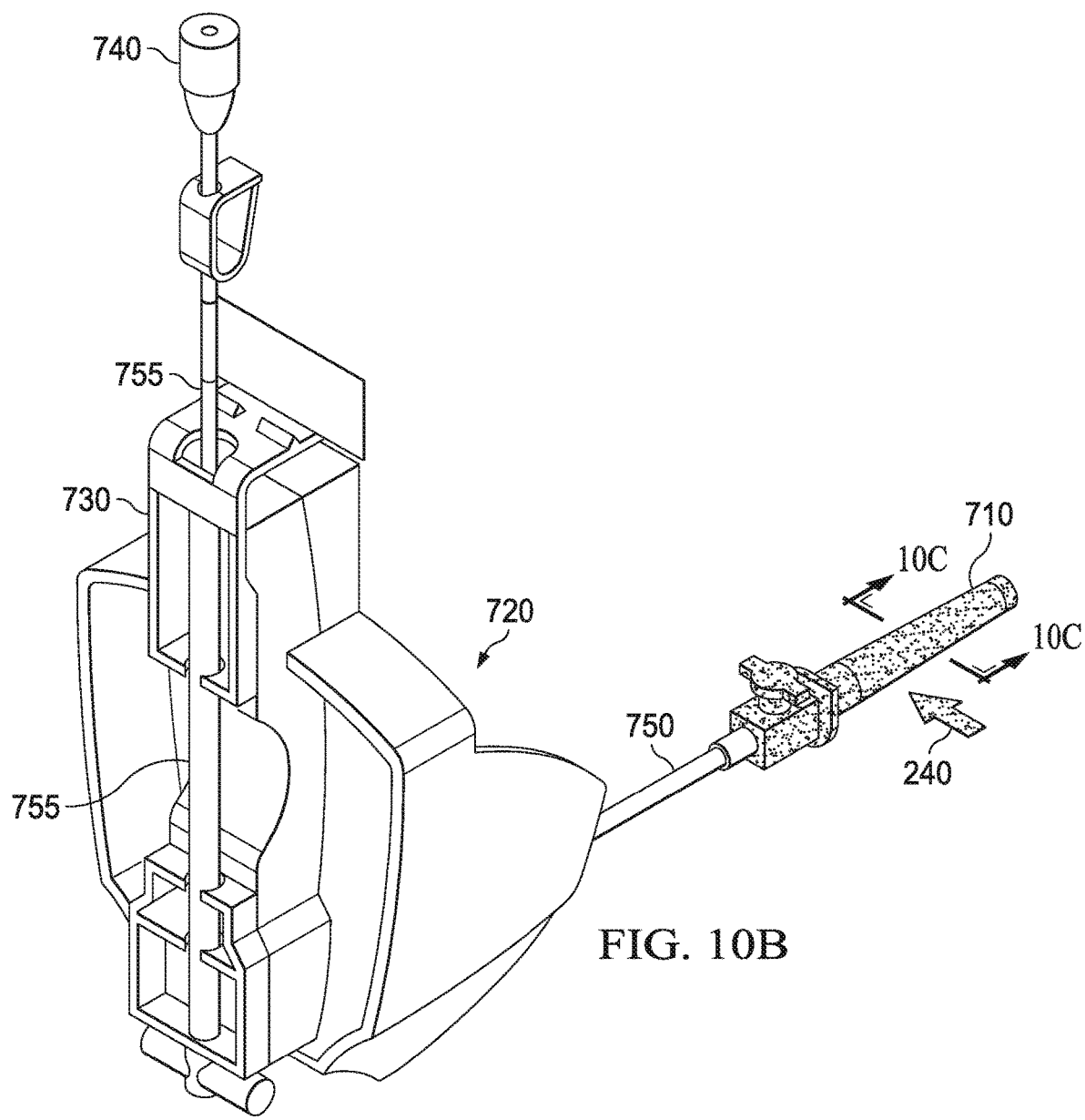
Figure 10C:
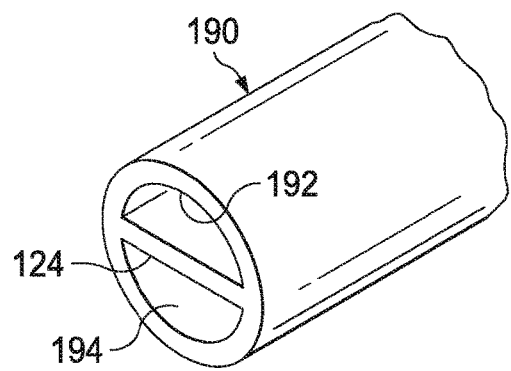
FIG. 10C is a sectional view of an example embodiment of a multi-lumen tubing spike that may be associated with the tubing spikes of FIGS. 10A-10B.

FIG. 10A and FIG. 10B are diagrams illustrating additional details that may be associated with some embodiments of the therapy unit 500. As illustrated in the embodiment of FIG. 10A and FIG. 10B, the thermoelectric module 124 may be thermally coupled to a tubing spike 710. For example, the thermoelectric module 124 may be inserted into the tubing spike 710. The thermoelectric module 124 may be configured to transfer heat energy 240 to the fluid 310 flowing through the tubing spike 710; additionally or alternatively the thermoelectric module 124 may be configured to extract heat energy 230 from the fluid 310 flowing through the tubing spike 710. In the example of FIG. 10A, the thermoelectric module 124 is configured to extract heat energy 230 from the fluid 310, and in the example of FIG. 10B, the thermoelectric module 124 is configured to transfer heat energy 230 to the fluid 310. FIG. 10C is a vertical sectional view of a multi-lumen tubing spike 710 that may be associated with some embodiments of the tubing spikes 710 depicted in FIG. 10A and FIG. 10B. The cutting plane of FIG. 10C shows the interior construction of the multi-lumen tubing spike 710, specifically, the relative locations of lumen 192, thermoelectric module 124, and lumen 194.

FIG. 11 is an illustrative table of test results for cell cultures exposed to a temperature-contrast therapy process in accordance with this specification. Column 1220 shows Adult Human Dermal Fibroblasts (HDFa) coverage relative to the starting percentage (%) cell coverage of 100 on Day 0 if treated with a 25° C. media. Column 1210 shows HDFa coverage relative to the starting percentage (%) cell coverage of 100 on Day 0 if treated with a 4° C. media. Column 1230 shows the temperature-contrast therapy process time in hours and minutes based upon a 24 hour clock format. Column 1240 shows the percentage (%) cell coverage for HDFa treated with 4° C. media. Column 1250 shows the percentage (%) cell coverage for HDFa treated with a 25° C. media. Column 1270 shows the time at which each respective HDFa was treated with a media and allowed to equate back to 37° C.

The test results of FIG. 11 were obtained as part of a temperature-contrast therapy feasibility study performed on cell cultures in the controlled environmental conditions of a research laboratory by the Inventors. Temperature-contrast therapy feasibility studies are normally performed over one or more days and include a number of process steps. The results depicted in FIG. 11 are for a temperature-contrast therapy feasibility study that was conducted over a period of 5 days and included the following processes and observations:

On Day 0, 1246, Adult Human Dermal Fibroblasts (HDFa) was seeded at about 150,000 cells per flask. A 25° C. media was added to one set of flasks and allowed to equilibrate to 37° C. over a period of 2 to 3 hours. A 4° C. media was also added to a second set of flasks and allowed to equilibrate to 37° C. over a period of 2 to 3 hours.

Prior to treatment on Day 1, 1248 cell coverage for HDFa treated with the 25° C. media was observed to be 13.8%, 1242 and cell coverage for HDFa treated with the 4° C. media was observed to be 12.1%, 1244.

On Day 1, 1248, the 25° C. media was added to the first set of flasks and allowed to equilibrate to 37° C. over a period of 2 to 3 hours. This process was repeated four times, 1246 over the course of day 1. The 4° C. media was added to the second set of flasks and allowed to equilibrate to 37° C. over a period of 2 to 3 hours. This process was repeated four times over the course of day 1 1248.

On Day 2, 1252, the 25° C. media was added to the first set of flasks and allowed to equilibrate to 37° C. over a period of 2 to 3 hours. This process was repeated three times over the course of day 2. The 4° C. media was added to the second set of flasks and allowed to equilibrate to 37° C. over a period of 2 to 3 hours. This process was repeated three times over the course of day 2, 1252.

On Day 3, 1254, the 25° C. media was added to the first set of flasks and allowed to equilibrate to 37° C. over a period of 2 to 3 hours. The 4° C. media was added to the second set of flasks and allowed to equilibrate to 37° C. over a period of 2 to 3 hours.

On Day 4, 1256, the 25° C. media was added to the first set of flasks and allowed to equilibrate to 37° C. over a period of 2 to 3 hours. The 4° C. media was added to the second set of flasks and allowed to equilibrate to 37° C. over a period of 2 to 3 hours.

On Days 5 through 7, 1258, 1260, and 1262 no media treatment was performed.

It was observed that while there was not a significant difference in the percentage (%) of cellular coverage, 65.7%, 1264 versus 67.8%, 1266, between HDFa treated with the 4° C. media and HDFa treated with the 25° C. media after 7 Days, 1262, there was a significant difference in the percentage (%) of cellular coverage over the course of Day 1, 1248 and Day 2, 1252.

In the example of FIG. 12, HDFa cells in a culture that were periodically treated with the 4° C. media and then allowed to equilibrate back to 37° C. for 2 to 3 hours induced a cellular activation response 1268 when compared to cells that were treated with the 25° C. media and allowed to equilibrate back to 37° C. over the course of Day 1, 1248 and Day 2, 1252.

This cellular activation response 1268 may be induced at a tissue site using the apparatus and processes described herein. For example, a dressing 102 including a porous pad may be applied to a tissue site and the combination may be covered by a sealing drape. The porous pad may be fluidly coupled to a thermoelectric module 124 and the thermoelectric module 124 may heat and/or cool the fluid 310, and thereby the tissue. This process may induce the cellular activation response 1268 noted above and/or the macro-mechanism temperature-contrast therapy action as disclosed herein at the tissue site.

The systems, apparatuses, and methods described herein may provide significant advantages. For example, temperature-contrast therapy process alone or in combination with negative-pressure therapy, with instillation therapy, or both, may speed up the inflammatory recovery process allowing for normal progression through the tissue healing trajectory. This may augment and accelerate growth of new tissue at the tissue site and reduce healing times. It may also be used to treat complications, such as a tissue infection and/or a tissue site with poor perfusion, which may be caused by inadequate blood supply to the capillary bed. Such complications, particularly in elderly patients or patients with severe comorbidities may develop into chronic ulcers that require medical intervention without the application of one or more of the therapy processes disclosed herein.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for stimulating healing of tissue at a tissue site, comprising:
    a dressing configured to be positioned at the tissue site;
    a source of therapeutic fluid;
    a first heat exchange chamber having a fluid inlet fluidly coupled to the source of therapeutic fluid and a fluid outlet fluidly coupled to the dressing;
    a second heat exchange chamber having a fluid inlet fluidly coupled to a second fluid source, the second fluid source being substantially the same as the source of therapeutic fluid and a fluid outlet configured to drain into the source of therapeutic fluid; and
    a thermoelectric module thermally coupled with the first heat exchange chamber and the second heat exchange chamber, the thermoelectric module adapted to transfer heat between the first heat exchange chamber and the second heat exchange chamber to provide therapeutic fluid from the source of therapeutic fluid alternating between a first temperature and a second temperature.

2. The system of claim 1, wherein the thermoelectric module comprises a first thermal transfer surface thermally coupled to the first heat exchange chamber and a second thermal transfer surface thermally coupled to the second heat exchange chamber.

3. The system of claim 1, wherein the thermoelectric module comprises a substantially tubular member, wherein the substantially tubular member has a first thermal transfer surface adapted to be thermally coupled to the first heat exchange chamber and a second thermal transfer surface adapted to be thermally coupled to the second heat exchange chamber.

4. The system of claim 3, wherein the first thermal transfer surface is an inner surface of the substantially tubular member and the second thermal transfer surface is an outer surface of the substantially tubular member.

5. The system of claim 3, wherein the first thermal transfer surface is an outer surface of the substantially tubular member and the second thermal transfer surface is an inner surface of the substantially tubular member.

6. The system of claim 1, wherein the thermoelectric module is configured to transfer heat between the first heat exchange chamber and the second heat exchange chamber in response to an application of power from a DC power source.

7. The system of claim 6, further comprising a temperature sensor thermally coupled to a fluid path between the dressing and the source of therapeutic fluid, the temperature sensor having an output signal indicative of a temperature at the tissue site.

8. The system of claim 7, further comprising a controller electrically coupled to the temperature sensor and the thermoelectric module, the controller comprising a temperature controller that compares the output signal to a target temperature, wherein the target temperature includes a hysteresis control band, wherein the controller is configured to maintain the output signal within the hysteresis control band.

9. The system of claim 7, further comprising a controller electrically coupled to the temperature sensor and the thermoelectric module, the controller comprising a temperature proportional-integral-derivative controller configured for a comparison between the output signal and a target temperature and to vary the power applied to the thermoelectric module based upon the comparison.

10. The system of claim 9, wherein the controller is configured to periodically cycle the target temperature between the first temperature and the second temperature over a therapeutic time period.

11. The system of claim 10, wherein the controller is configured to maintain the first temperature and the second temperature for a fixed period of time, wherein the fixed period of time is between 1 and 30 minutes.

12. The system of claim 10 wherein the controller is configured to reduce the temperature at the tissue site if the output signal is greater than the second temperature and increase the temperature at the tissue site if the output signal is less than the first temperature.

* * * * *